US006808899B2

(12) United States Patent
Matsumoto et al.

(10) Patent No.: US 6,808,899 B2
(45) Date of Patent: Oct. 26, 2004

(54) POLYNUCLEOTIDES ENCODING SREB3 RECEPTOR

(75) Inventors: Mitsuyuki Matsumoto, Ibaraki (JP); Toru Sugimoto, Ibaraki (JP); Jun Takasaki, Ibaraki (JP); Masazumi Kamohara, Ibaraki (JP); Tetsu Saito, Ibaraki (JP); Masato Kobayashi, Tokyo (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 45 days.

(21) Appl. No.: 10/318,142

(22) Filed: Dec. 13, 2002

(65) Prior Publication Data

US 2003/0077662 A1 Apr. 24, 2003

Related U.S. Application Data

(62) Division of application No. 09/622,439, filed as application No. PCT/JP99/01191 on Mar. 11, 1999, now Pat. No. 6,555,334.

(30) Foreign Application Priority Data

Mar. 12, 1998 (JP) ....................................... P. 10-060245
Feb. 3, 1999 (JP) ....................................... P. 11-026774

(51) Int. Cl.$^{7}$ ......................... C12P 23/00; C12N 15/00; C12N 5/00; C12N 1/20; C12Q 1/16

(52) U.S. Cl. .................. 435/69.1; 435/69.1; 435/320.1; 435/325; 435/252.3; 435/35; 435/7.21; 536/23.5; 530/350

(58) Field of Search ................................ 435/69.1, 7.1, 435/320.1, 325; 536/23.5; 530/350

(56) References Cited

U.S. PATENT DOCUMENTS 5,508,384 A 4/1996 Murphy
6,071,722 A 6/2000 Elshourbagy et al.

FOREIGN PATENT DOCUMENTS

WO WO 99/55733 A 11/1999
WO WO 00/22131 4/2000
WO WO 00/31258 6/2000

OTHER PUBLICATIONS

Morin et al, *Mol. Cell. Biol., 21(4)*: 1036–1044 (2001).
Fromm et al, *PNAS, 94*:10098–10103 (1997).
Herman et al, *JBC, 270(19)*:11654–11661 (1995).
Sheriff et al, *JPET, 51*:597–604 (1997).
Pende et al, *J. Neurosci., 17(4)*:1291–1301 (1997).
White et al, *PNAS, 97(25)*:13967–13972 (2000).
Shi et al, *JBC, 32(11)*:24470–24476 (2000).
Mao et al, *JBC, 42(16)*:27118–27123 (1998).
Feng et al, *J. Neurosci., 16(12)*:3925–3933 (1996).
O'Dowd et al, *Genomics*, Int. J. for Analyses of the Human and Other Genomes, vol. 47, No. 2 (Jan. 15, 1998).
Brenner, *Trends Genetics, 15(4)*:132–133 (1999).
Bork, *Trends Genetics, 12(10)*:425–427 (1996).
Bork, *Genome Res., 10*:398–400 (2000).
Doerks et al, *Trends Genetics, 14(6)*:248–250 (1998).
Sholnick, *Trends Biotech., 18(1)*:34–39 (2000).
Smith, *Bioinformatics, 15*:1222–1223 (1997).
Wess, *FASEB J., 11*:346–354 (1997).
Matsumoto et al, *Biochemical and Biophysical Res. Comm., 272*:576–582 (2000).

*Primary Examiner*—Elizabeth Kemmerer
*Assistant Examiner*—Sandra Wegert
(74) *Attorney, Agent, or Firm*—Sughrue Mion, PLLC

(57) ABSTRACT

This invention belongs to the genetic engineering field, and provides novel G protein-coupled receptor family proteins SREB1, SREB2 and SREB3 expressed in the central nervous system, genes coding for these proteins, screening methods using these proteins and so on. As one of the methods for obtaining the G protein-coupled receptor proteins of the present invention, RT-PCR is carried out using mRNA extracted from human or rat brain tissue or brain-derived cells as the template and using two primers interposing the entire portion or a part of the G protein-coupled receptor protein translation region, thereby obtaining cDNA corresponding to the G protein-coupled receptor protein or a part thereof, and the cDNA is integrated into an appropriate expression vector and expressed in a host cell.

8 Claims, 10 Drawing Sheets

FIG. 1

```
SREB 1  MANASEPGGSGGGEAAALG----LKLATLSLLLCVSLAGN  35
SREB 2  MANYSHAADNILQNLSP--LTAFLKLTSLGFIIGVSVVGN  38
SREB 3  MANTTGEPEEVSGALSLPSASAYVKLVLLGLIMCVSLAGN  40

SREB 1  VLFALLIVRERSLHRAPYYLLLDLCLADGLRALACLPAVM  76
SREB 2  LLISILLVKDKTLHRAPYYFLLDLCCSDILRSAICFPFVF  78
SREB 3  AILSLLVLKERALHKAPYYFLLDLCLADGIRSAVCFPFVL  80

SREB 1  LAARRAAAAAGAPPGALGCKLLAFLAALFCFHAAFLLLGV  116
SREB 2  NSVKNGSTWTY---GTLTCKVIAFLGVLSCFHTAFMLFCI  115
SREB 3  ASVRHGSSWTF---SALSCKIVAFMAVLFCFHAAFMLFCI  117

SREB 1  GVTRYLAIAHHRFYAERLAGWPCAAMLVCAAWALALAAAF  156
SREB 2  SVTRYLAIAHHRFYTKRLTFWTCLAV-ICMVWTLSVAMAF  154
SREB 3  SVTRYMAIAHHRFYAKRMTLWTCAAV-ICMAWTLSVAMAF  156

SREB 1  PPVLDVGG---DDEDAPCALEQRPDGAPGALGFLLLLAVV  193
SREB 2  PPVLDVGTYSFIREEDQCTFQHRSFRANDSLGFMLLLALI  194
SREB 3  PPVFDVGTYKFIREEDQCIFEHRYFKANDTLGFMLMLAVL  196

SREB 1  VGATHLVYLRLLFFIHDRRKMRPARLVPAVSHDWTFHGPG  233
SREB 2  LLATQLVYLKLIFFVHDRRKMKPVQFVAAVSQNWTFHGPG  234
SREB 3  MAATHAVYGKLLLFEYRHRKMKPVQMVPAISQNWTFHGPG  236

SREB 1  ATGQAAANWTAGFGRGPTPPALVGIRPAGPGRGARRLLVL  273
SREB 2  ASGQAAANWLAGFGRGPTPPTLLGIRQNANTTGRRRLLVL  274
SREB 3  ATGQAAANWIAGFGRGPMPPTLLGIRQNGHAASRR-LLGM  275

SREB 1  EEFKTEKRLCKMFYAVTLLFLLLWGPYVVASYLRVLVRPG  313
SREB 2  DEFKMEKRISRMFYIMTFLFLTLWGPYLVACYWRVFARGP  314
SREB 3  DEVKGEKQLGRMFYAITLLFLLLWSPYIVACYWRVFVKAC  315

SREB 1  AVPQAYLTASVWLTFAQAGINPVVCFLFNRELRDCFRAQF  353
SREB 2  VVPGGFLTAAVWMSFAQAGINPFVCIFSNRELRRCFSTTL  354
SREB 3  AVPHRYLATAVWMSFAQAAVNPIVCFLLNKDLKKCLRTHA  355

SREB 1  PCCQSPRTTQATHP--CDLKGIGL.  (SEQ ID NO:2)  376
SREB 2  LYCRKS---RLPREPYC------VI.  (SEQ ID NO:4)  371
SREB 3  P-CWGTGGAPAPREPYC------MM.  (SEQ ID NO:6)  374
```

Figure 2:
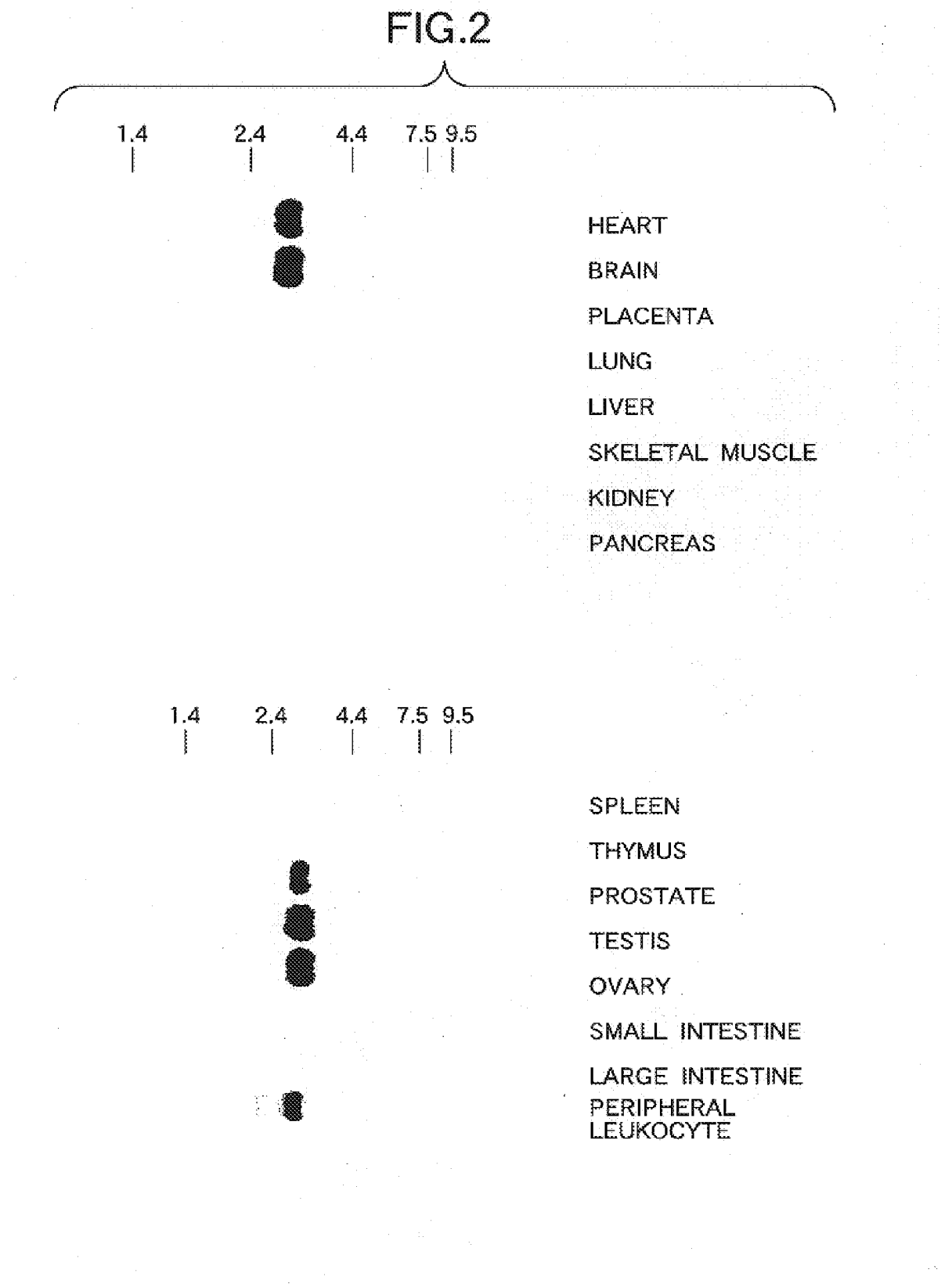

HEART
BRAIN
PLACENTA
LUNG
LIVER
SKELETAL MUSCLE
KIDNEY
PANCREAS 1.4 2.4 4.4 7.5 9.5

SPLEEN
THYMUS
PROSTATE
TESTIS
OVARY
SMALL INTESTINE
LARGE INTESTINE
PERIPHERAL LEUKOCYTE

Figure 3:
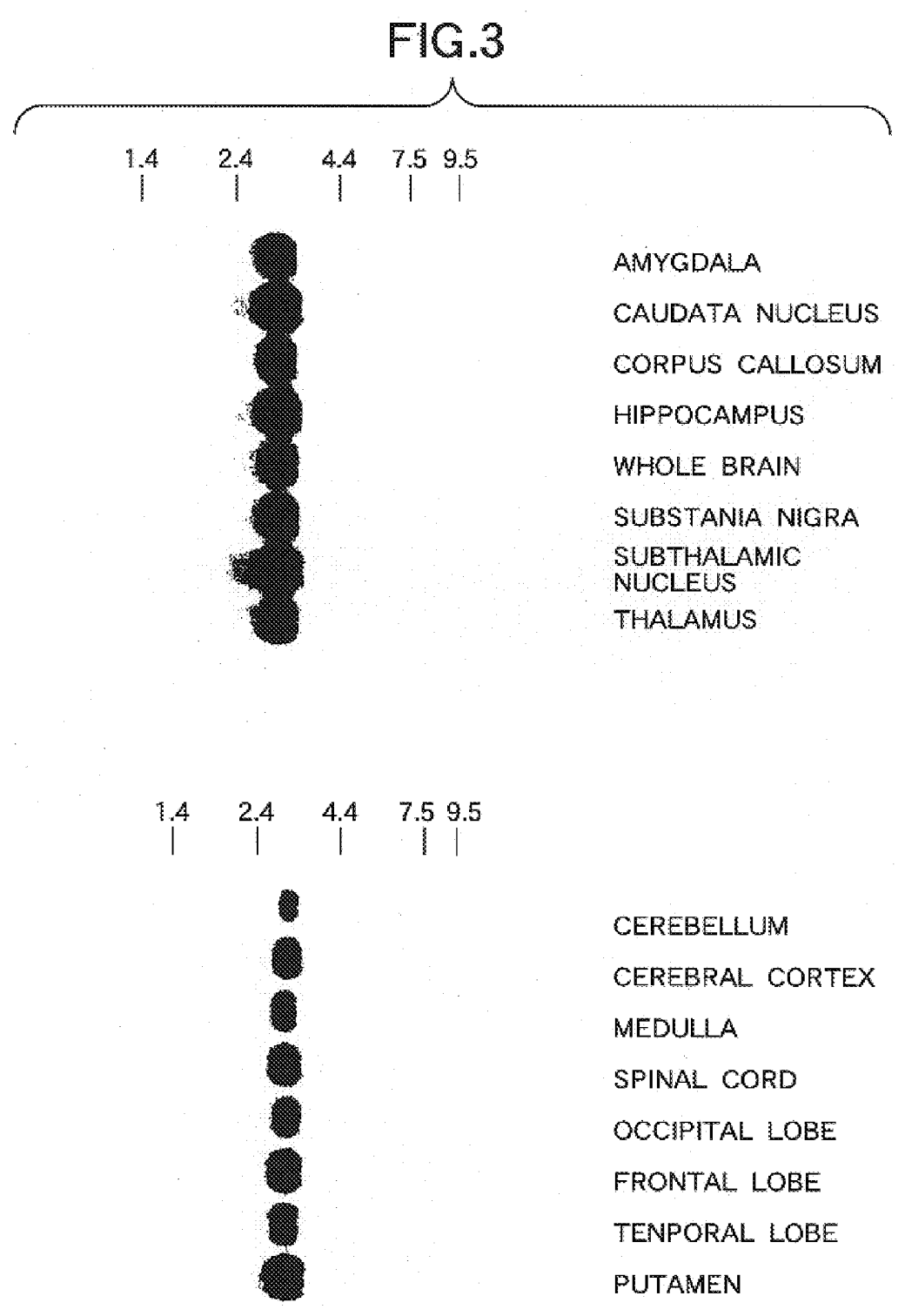

AMYGDALA
CAUDATA NUCLEUS
CORPUS CALLOSUM
HIPPOCAMPUS
WHOLE BRAIN
SUBSTANIA NIGRA
SUBTHALAMIC NUCLEUS
THALAMUS 1.4 2.4 4.4 7.5 9.5

CEREBELLUM
CEREBRAL CORTEX
MEDULLA
SPINAL CORD
OCCIPITAL LOBE
FRONTAL LOBE
TENPORAL LOBE
PUTAMEN 1.4 2.4 4.4 7.5 9.5

HEART
BRAIN
PLACENTA
LUNG
LIVER
SKELETAL MUSCLE
KIDNEY
PANCREAS 1.4 2.4 4.4 7.5 9.5

SPLEEN
THYMUS
PROSTATE
TESTIS
OVARY
SMALL INTESTINE
LARGE INTESTINE
PERIPHERAL LEUKOCYTE

FIG.5
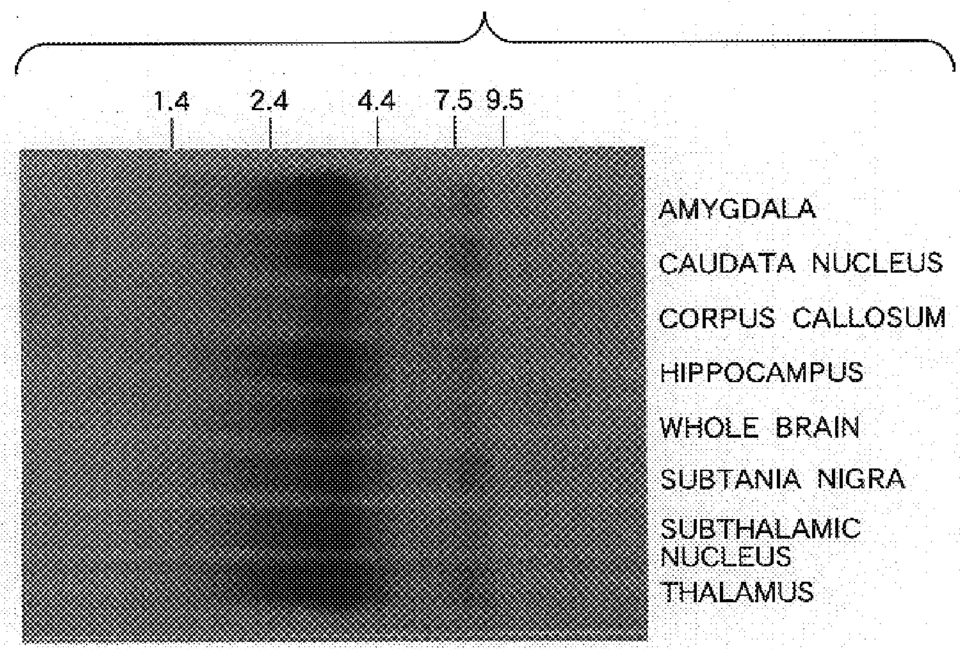
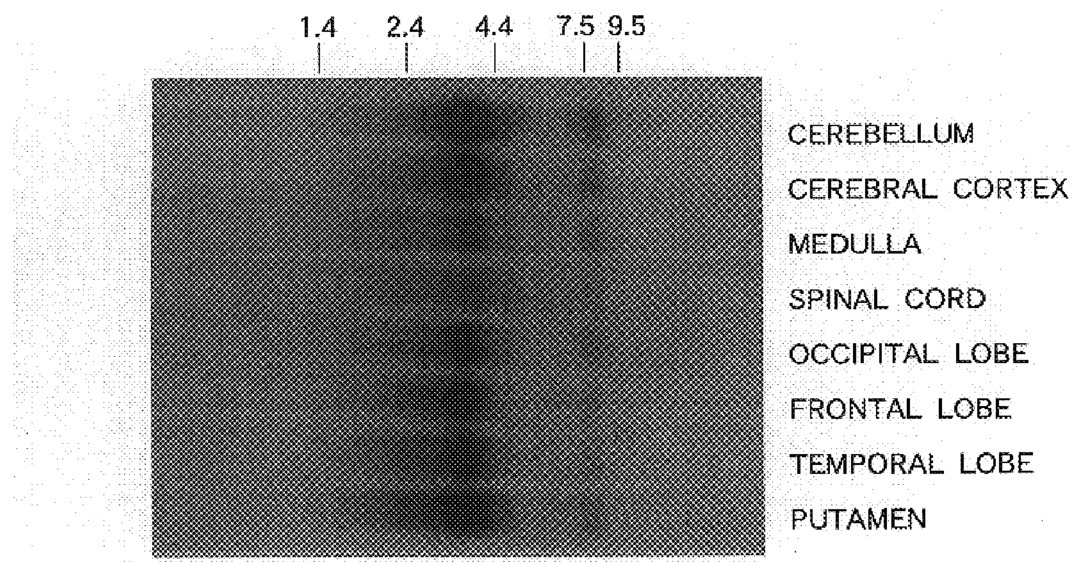

FIG.7
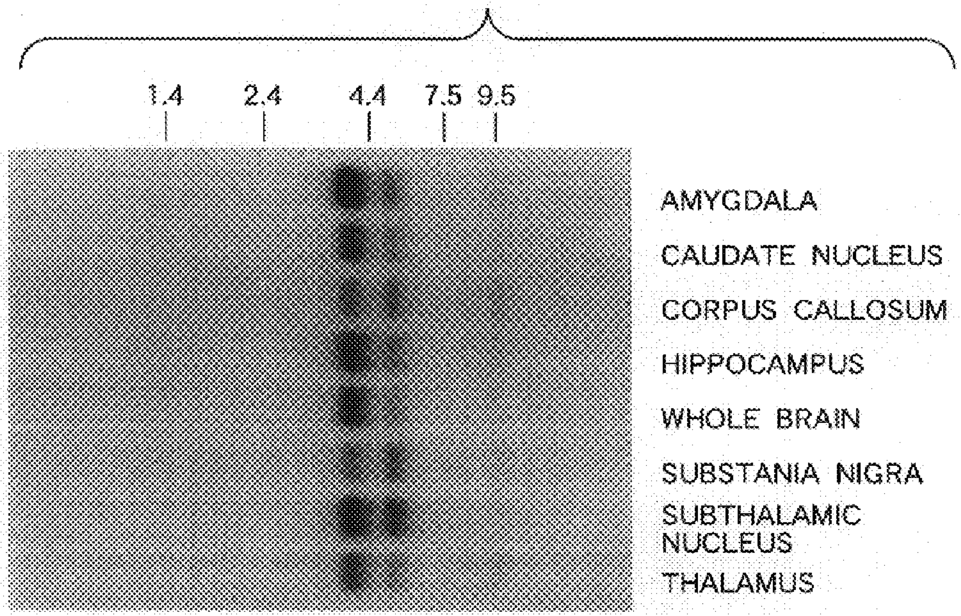
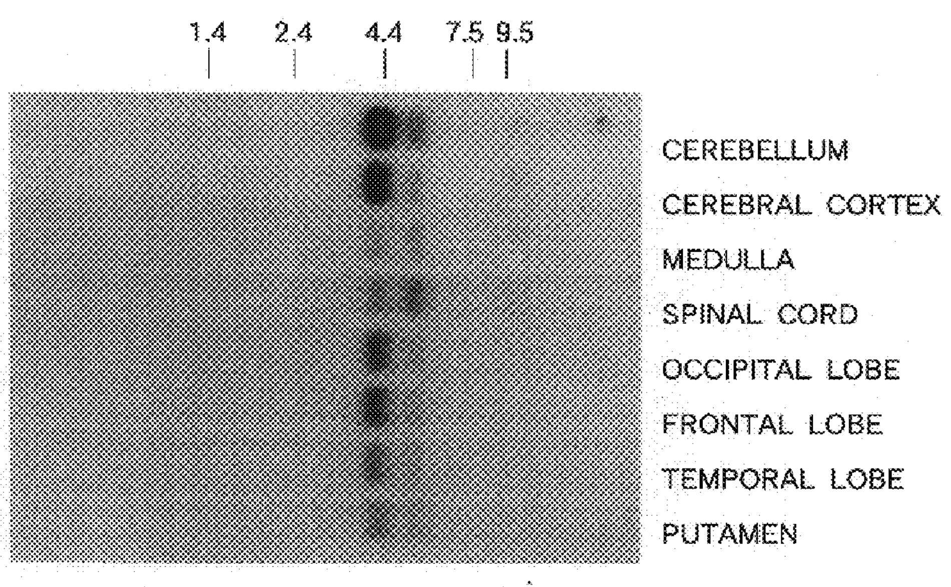

POLYNUCLEOTIDES ENCODING SREB3 RECEPTOR

This Application is a Divisional of U.S. application Ser. No. 09/622,439, filed Aug. 17, 2000, now U.S. Pat. No. 6,555,344 which is a 371 of PCT/JP99/01191, filed Mar. 11, 1999, the disclosure of each of which is incorporated herein by reference.

TECHNICAL FIELD

This invention belongs to the genetic engineering field, and relates to novel G protein-coupled receptor proteins, genes coding for these G protein-coupled receptor proteins, methods for producing these G protein-coupled receptor proteins, screening methods using these G protein-coupled receptor proteins, antibodies for these G protein-coupled receptor proteins and screening methods using these antibodies.

BACKGROUND ART

Cell membrane receptors which transmit signals to the intracellular region via the activation of heterotrimeric GTP binding protein are generally referred to as "G protein-coupled receptor". All members of the G protein-coupled receptor known to date are sometimes referred generally to as "seven transmembrane receptor", because they form a super family having a common structure which has the extracellular amino terminus and intracellular carboxyl terminus and passes through the cell membrane seven times. The G protein-coupled receptor transmits information on various physiologically active substances from cell membranes to the intracellular region via activation of heterotrimeric GTP binding protein and subsequent changes in the intracellular second messengers induced. As the intracellular second messengers which are controlled by the heterotrimeric GTP binding protein, cAMP via adenylate cyclase, $Ca^{++}$ via phospholipase C and the like are well known, and it has been revealed recently that many cellular proteins are their targets, such as the control of channels and activation of protein kinases via the heterotrimeric GTP binding protein (Gudermann, T. et al. (1997), *Annu. Rev. Neurosci.,* 20, 399–427). The physiologically active substances that transmit information via the G protein-coupled receptor include various known physiologically active substances such as neurotransmitters, hormones, chemokine, lipid-originated signal transducers, divalent ions and proteases. Information by these physiologically active substances is transmitted to the intracellular region through their specific G protein-coupled receptor, respectively.

Several hundred types of G protein-coupled receptor have so far been cloned from eucaryote. Regarding human, hundred or more types of G protein-coupled receptor for corresponding endogenous ligands have been cloned and are regarded as targets of drugs for diseases. There are various diseases in which G protein-coupled receptor is the target, and there exist effective drugs which act upon G protein-coupled receptor, in the respective fields of central nervous system, circulatory organ system, inflammatory immune system, digestive organ system, motor organ system and urinary organ/reproductive organ system (Stadel, J. et al. (1997), *Trends Pharmacol. Sci.,* 18, 430–437). This indicates that agonists or antagonists of G protein-coupled receptor have a high possibility of becoming a therapeutic agent of diseases, so that studies are being actively carried out on the discovery and identification of new G protein-coupled receptors.

Cloning of G protein-coupled receptor genes tends to start based on their structural homology in the super family in many cases, and a receptor having no correspondence to endogenous ligand is referred to as "the orphan G protein-coupled receptor". In general, a ligand specific for the orphan G protein-coupled receptor has not been found, so that it was difficult to develop its agonist or antagonist. In recent years, however, it has been proposed to create a drug targeting for the orphan G protein-coupled receptor by combining the substantiated compound libraries and high performance high throughout screening (Stadel, J. et al. (1997), *Trends Pharmacol. Sci.,* 18, 430–437).

That is, it is possible to screen an agonist for an orphan G protein-coupled receptor from a compound library by effective high throughput system of the measurement of cAMP and $Ca^{++}$ which are second messengers of many G protein-coupled receptors, or the measurement of GTPase activity and G protein binding of GTPγS which are indexes of the activation of heterotrimeric GTP binding protein, so that it is possible to find specific agonists and antagonists making use of such compounds and furthermore to develop therapeutic drugs for certain diseases. Under such conditions, discovery of a novel G protein-coupled receptor capable of becoming a new therapeutic target of diseases is regarded as the most important step in creating a medicament which acts upon G protein-coupled receptors.

Among G protein-coupled receptors, there is a case in which a plurality of receptors are present for one endogenous ligand. Such receptors are referred to as receptor family, and each receptor is called subtype. Since all of the G protein-coupled receptors have a common structure which passes through the cell membrane seven times, 20 to 25% of amino acids are preserved mainly in the transmembrane region even in mutually independent G protein-coupled receptors, but when they form a receptor family, ratio of the amino acids preserved among its subtypes significantly increases to 35% or more, particularly to 60 to 80% among subtypes having high relevancy (Strader, C. D. et al. (1994), *Annu. Rev. Biochem.,* 63, 101–132).

When development of a therapeutic drug for diseases is planned by targeting for an endogenous ligand wherein a receptor family is present, specificity of its subtypes becomes important in many cases. This is because actions upon other subtype than actions upon a subtype that mediates the main action of a drug lead to side effects in many cases. Accordingly, it is desirable to create a subtype-specific agonist or antagonist, but it is necessary to find a means for detecting the subtype-specificity for that purpose. Currently, a method for constructing a system in which a gene of a subtype is cloned and its specificity is detected using a cultured cell line or the like which expresses the gene is generally used.

When a novel G protein-coupled receptor is used as the target of disease treatment, it is highly possible that the subtype-specificity is important, so that discovery of a receptor family is important also in the case of the novel G protein-coupled receptor. The homology of amino acid sequences among independent G protein-coupled receptors is 20 to 25% as a whole, but when they form a receptor family, the homology significantly increases in general in the family; so that it is possible to presume whether they form a family or not, by comparing homology between two G protein-coupled receptors. It is possible to find novel G protein-coupled receptors which form a family, making use of such a means, and when a novel G protein-coupled receptor family is discovered, it will open a way for developing a drug for disease therapy because of the possibility of creating a subtype-specific agonist or antagonist.

The central nervous system transmits and controls various kinds of information using physiologically active substances represented by neurotransmitters. The G protein-coupled receptor is taking an important role in the signal transduction and control. Since many types of G protein-coupled receptor are present in the central nervous system, they are used as important therapeutic targets for diseases of the central nervous system. For example, it is considered that the G protein-coupled receptor of a neurotransmitter, dopamine, is a therapeutic target of schizophrenia (Seeman, P. et al. (1997), *Neuropsychopharmacology,* 16, 93–110), the G protein-coupled receptor of serotonin is that of depression (Cowen, P. J. (1991), *Br. J. Psychiatry,* 159 (Suppl. 12), 7–14), and the G protein-coupled receptor of neuro-peptide Y is that of eating disorder (Blomqvist, A. G. and Herzog, H. (1997), *Trends Neurosci.,* 20, 294–298).

It is considered that a novel G protein-coupled receptor expressing in the central nervous system, preferably a human receptor, will lead to a candidate for a new therapeutic target of central nervous system diseases or to the elucidation of central nervous system functions. In addition, for the purpose of developing a subtype-specific drug, it is desirable also to find a family in the case of the novel G protein-coupled receptor expressing in the central nervous system. Though the gene of a receptor GPR27 obtained from a mouse, having high homology with the amino acid sequence of SREB1 which is one of the G protein-coupled receptors of the invention, and an amino acid sequence based on its gene sequence have been reported (O'Dowd, B. F. et al. (1998), *Genomics,* 47, 310–313), no information is available to date concerning gene sequence and amino acid sequence of a human receptor.

DISCLOSURE OF THE INVENTION

The present invention is to provide novel G protein-coupled receptor family proteins expressed in the central nervous system, as the target of therapeutic agents for central nervous system diseases.

With the aim of achieving the above object, the present inventors have conducted intensive studies and, as a result, succeeded in isolating genes (SREB1, SREB2, SREB3, rSREB1, rSREB2 and rSREB3) which encode novel G protein-coupled receptor family proteins expressed in the central nervous system.

Also, we have established vectors containing these genes, host cells containing these vectors and methods for producing these G protein-coupled receptor proteins using such host cells, and rendered possible screening of these G protein-coupled receptor proteins and compounds, peptides and antibodies capable of modifying activities of the G protein-coupled receptor proteins.

Illustratively, the present invention relates to (1) a G protein-coupled receptor protein which has the amino acid sequence described in SEQ ID NOs: 2, 4, 6, 22 or 26, or a G protein-coupled receptor protein as an equivalent to the protein, preferably a human origin G protein-coupled receptor protein which has the amino acid sequence described in SEQ ID NOs: 2, 4 or 6 or a G protein-coupled receptor protein as an equivalent to the protein, or a rat origin G protein-coupled receptor protein which has the amino acid sequence described in SEQ ID NOs: 6, 22 or 26 or a G protein-coupled receptor protein as an equivalent to the protein, (2) a G protein-coupled receptor protein which has the amino acid sequence described in SEQ ID NOs: 2, 4, 6, 22 or 26, (3) a gene which has a nucleotide sequence coding for the G protein-coupled receptor protein described in the item (1), (4) a vector which contains the gene described in the item (3), (5) a host cell which contains the vector described in the item (4), (6) a method for producing the G protein-coupled receptor protein described in the item (1) or (2), or a G protein-coupled receptor protein as an equivalent to the protein, which comprises using the host cell described in the item (5), (7) a method for screening a medicament acting on the G protein-coupled receptor protein described in the item (1) or (2), which comprises allowing the G protein-coupled receptor protein to contact with a compound to be tested, or (8) an antibody for the G protein-coupled receptor protein described in the item (1) or (2) or a partial peptide thereof.

The following explains the terms to be used herein.

The term "human origin" or "rat origin" means an amino acid sequence identical to the amino acid sequence of a G protein-coupled receptor protein expressing in human or rat.

The term "equivalent" of the G protein-coupled receptor protein of the present invention means a G protein-coupled receptor protein which is expressed in the central nervous system and shows the same activity of any one of the G protein-coupled receptor proteins represented by the amino acid sequences described in SEQ ID NOs: 2, 4, 6, 22 or 26.

In this connection, the G protein-coupled receptor and the G protein-coupled receptor protein have the same meaning.

The novel G protein-coupled receptor protein of the present invention is any one of the G protein-coupled receptor proteins represented by the amino acid sequences described in SEQ ID NOs: 2, 4, 6, 22 and 26, or equivalents thereof. Illustratively, all of G protein-coupled receptor proteins are included in the invention as long as they have the amino acid sequence described in SEQ ID NOs: 2, 4, 6, 22 or 26, or an amino acid sequence in which the amino acid sequence described in SEQ ID NOs: 2, 4, 6, 22 or 26, has substitution, deletion or insertion of one or a plurality, preferably from 1 to 10, more preferably from 1 to 7, most preferably from 1 to 5, of amino acids, and have the same activity of the protein represented by the amino acid sequence described in SEQ ID NOs: 2, 4 or 6. Preferably, it is a human or rat origin G protein-coupled receptor protein having the amino acid sequence described in SEQ ID NOs: 2, 4, 6, 22 or 26.

Also, the gene which has a nucleotide sequence coding for the novel G protein-coupled receptor protein of the invention may be any gene, as long as it has a nucleotide sequence coding for the G protein-coupled receptor protein represented by the amino acid sequence described in SEQ ID NOs: 2, 4 or 6, or an equivalent thereof. Preferably, it is a gene which has a nucleotide sequence coding for the amino acid sequence described in SEQ ID NOs: 2, 4, 6, 22 or 26. More preferably, it is a gene which has a sequence of from 1 to 1,125 positions of the nucleotide sequence described in SEQ ID NO: 1, from 1 to 1,110 positions of the nucleotide sequence described in SEQ ID NO: 3, from 1 to 1,119 positions of the nucleotide sequence described in SEQ ID NO: 5, from 1 to 1,131 positions of the nucleotide sequence described in SEQ ID NO: 21, from 1 to 1,110 positions of the nucleotide sequence described in SEQ ID NO: 23 or from 1 to 1,119 positions of the nucleotide sequence described in SEQ ID NO: 25.

The gene which encodes the G protein-coupled receptor protein of the invention can be obtained by the following methods.

1) Production Methods of Novel G Protein-Coupled Receptor Protein Gene a) First Production Method A mRNA sample is extracted from human cells or tissue having the ability to produce the G protein-coupled receptor protein of the invention. Next, using this mRNA as the template, two primers interposing the G protein-coupled receptor protein mRNA or a part of the mRNA region is prepared. The G protein-coupled receptor protein cDNA or a part thereof can be obtained by carrying out a reverse transcriptase-polymerase chain reaction (to be referred to as RT-PCR hereinafter) suited for SREB1, SREB2 or SREB3 by modifying the conditions for denature temperature, denaturing agent addition and the like. Thereafter, the receptor protein can be produced by integrating the thus obtained G protein-coupled receptor cDNA or a part thereof into an appropriate expression vector and expressing it in a host cell.

Firstly, mRNA molecules including those encoding the G protein-coupled receptor protein of the invention are extracted by a known method from cells or tissue, such as of the human brain or rat brain, having the ability to produce the protein. Regarding the extraction method, a guanidine thiocyanate hot phenol method, a guanidine thiocyanate-guanidine hydrochloride method and the like can be exemplified, and a guanidine thiocyanate cesium chloride method can be cited as a preferred method. The cells or tissue having the ability to produce the protein can be identified by the Northern blotting method using a gene having a nucleotide sequence coding for the protein or a part thereof or by the Western blotting method using an antibody specific for the protein.

Purification of mRNA can be carried out in accordance with the conventional method, for example by adhering the mRNA to an oligo(dT) cellulose column and then eluting it therefrom. In addition, the mRNA can be further fractionated, for example, by a sucrose density gradient centrifugation. Alternatively, a commercially available already-extracted mRNA preparation may be used without carrying out the mRNA extraction.

Next, a single-stranded cDNA is synthesized from the thus purified mRNA by carrying out a reverse transcriptase reaction in the presence of a random primer or an oligo-dT primer. This synthesis can be carried out in the conventional way. The novel G protein-coupled receptor DNA of interest is amplified by subjecting the thus obtained single-stranded cDNA to PCR using two primers interposing a region of the gene of interest. The thus obtained DNA is fractionated, for example, by an agarose gel electrophoresis. As occasion demands, a DNA fragment of interest can be obtained by digesting the DNA with restriction enzymes and then connecting the digests.

b) Second Production Method

In addition to the above method, the gene of the invention can also be produced making use of conventional genetic engineering techniques. Firstly, single-stranded cDNA is synthesized using the mRNA obtained by the above method as the template and a reverse transcriptase, and then double-stranded cDNA is synthesized from the single-stranded cDNA. Examples of the method include the S1 nuclease method (Efstratiadis, A. et al. (1976), *Cell,* 7, 279–288), the Land method (Land, H. et al. (1981), *Nucleic Acids Res.,* 9, 2251–2266), the O. Joon Yoo method (Yoo, O. J. et al. (1983), *Proc. Natl. Acad. Sci. USA,* 79, 1049–1053) and the Okayama-Berg method (Okayama, H. and Berg, P. (1982), *Mol. Cell. Biol.,* 2, 161–170).

Next, the recombinant plasmid obtained by the above method is introduced into an *Escherichia coli* strain, such as DH5α, to effect its transformation, and a transformant can be selected making use of tetracycline resistance or ampicillin resistance as a marker. For example, when the host cell is *Escherichia coli,* transformation of the host cell can be carried out by the Hanahan's method (Hanahan, D. (1983), *J. Mol. Biol.,* 166, 557–580), namely a method in which the recombinant DNA is added to competent cells prepared in the presence of $CaCl_2$ and $MgCl_2$ or RbCl. In this case, not only a plasmid but also a lambda or the like phage vector can also be used as the vector.

A strain having DNA coding for the novel G protein-coupled receptor protein of interest can be selected from the thus obtained transformants, for example by the following various methods.

(1) A Screening Method which Uses a Synthetic Oligonucleotide Probe

An oligonucleotide corresponding to the entire portion or a part of the G protein-coupled receptor protein of the invention is synthesized (in this case, it may be either a nucleotide sequence derived using the codon usage or a combination of plural possible nucleotide sequences, and in the latter case, their kinds can be reduced by including inosine), this is used as a probe (labeled with $^{32}P$ or $^{33}P$) and allowed to hybridize with DNA samples of transformants, which are denatured and fixed on a nitrocellulose filter, and then a positive strain is screened and selected.

(2) A Screening Method Which Uses a Probe Prepared by Polymerase Chain Reaction

Sense primer and antisense primer oligonucleotides corresponding to a part of the G protein-coupled receptor protein of the invention are synthesized, and polymerase chain reaction (Saiki, R. K. et al. (1988), *Science,* 239, 487–491) is carried out using a combination of them to effect amplification of a DNA fragment of interest coding for the entire portion or a part of the G protein-coupled receptor protein. As the template DNA to be used herein, cDNA synthesized by the reverse transcription reaction from mRNA of cells capable of producing the G protein-coupled receptor protein or genomic DNA can be used. The thus prepared DNA fragment is labeled with $^{32}P$ or $^{33}P$ and used as the probe to select a clone of interest by carrying out colony hybridization or plaque hybridization.

(3) A Screening Method in Which the Novel G Protein-coupled Receptor Protein is Produced in Other Animal Cells A transformant is cultured to amplify the gene of interest, the gene is transfected into an animal cell (in this case, either a plasmid which can perform autonomous replication and contains a transcription promoter region or a plasmid which can be integrated into chromosome of the animal cell may be used) and a protein coded by the gene is produced on the cell surface. By detecting the protein using an antibody specific for the G protein-coupled receptor protein of the invention, a strain of interest having cDNA coding for the G protein-coupled receptor protein is selected from the original transformants.

(4) A Selection Method Which Uses an Antibody Specific for the G Protein-coupled Receptor Protein of the Invention In advance, cDNA is integrated into an expression vector and protein is produced on the surface of transformant strains, and then strains capable of producing the G protein-coupled receptor protein are detected using an antibody specific for the G protein-coupled receptor protein of the invention and a second antibody for the first antibody, thereby selecting a strain of interest.

(5) A Method Which Uses a Selective Hybridization Translation System

Samples of cDNA obtained from transformants are blotted on, for example, a nitrocellulose filter and hybridized with mRNA prepared from cells capable of producing the G protein-coupled receptor protein of the invention, and then the mRNA linked to the cDNA is dissociated and recovered. The thus recovered mRNA is then translated into protein using a protein translation system, for example by injecting into Xenopus oocyte or in a cell-free system such as a rabbit reticulocyte lysate, wheat germ or the like. A strain of interest is selected by detecting it using an antibody for the G protein-coupled receptor protein of the invention.

Collection of DNA which encodes the G protein-coupled receptor protein of the invention from the thus obtained transformant of interest can be carried out in accordance with a known method (Maniatis, T. et al. (1982): "Molecular Cloning—A Laboratory Manual", Cold Spring Harbor Laboratory, NY). For example, it can be carried out by separating a fraction corresponding to a plasmid DNA from cells, and cutting out a cDNA region from the plasmid DNA.

c) Third Production Method

The gene which has a nucleotide sequence coding for the amino acid sequence represented by SEQ ID NOs: 2, 4, 6, 22 or 26 can also be produced by binding DNA fragments produced by a chemical synthesis method. Each DNA can be synthesized using a DNA synthesizer (e.g., Oligo 1000M DNA Synthesizer (Beckman), 394 DNA/RNA Synthesizer (Applied Biosystems) or the like).

d) Fourth Production Method

For the purpose of effecting expression of the function of G protein-coupled receptor protein of the invention by the substance thus obtained by genetic engineering techniques making use of the gene of the invention, it is not always necessary to have all of the amino acid sequences represented by SEQ ID NOs: 2, 4, 6, 22 and 26; for example, even if it is a partial sequence or other amino acid sequence is added thereto, such proteins are also included in the G protein-coupled receptor protein of the invention, as long as they show the same activity of the G protein-coupled receptor protein represented by the amino acid sequence shown in SEQ ID NOs: 2, 4, 6, 22 or 26. Also, as is known by the interferon gene and the like, it is considered that genes of eucaryote generally show polymorphism (e.g., see Nishi, T. et al. (1985), *J. Biochem.,* 97, 153–159), and there is a case in which one or a plurality of amino acid are substituted by this polymorphism or a case in which the nucleotide sequence is changed but the amino acids are completely unchanged. In consequence, even in the case of proteins in which one or a plurality of amino acid residues are substituted, deleted or inserted at one or a plurality of positions in the amino acid sequence represented by SEQ ID NOs: 2, 4 or 6, it is possible that they have the same activity of the G protein-coupled receptor represented by the amino acid sequence described in SEQ ID NOs: 2, 4 or 6. These proteins are called equivalents to the G protein-coupled receptor protein of the invention and included in the invention. In addition, a G protein-coupled receptor having the rat origin amino acid sequence shown by SEQ ID NOs: 22, 24 or 26 or a G protein-coupled receptor having the same activity of the former receptor is also included in the equivalents.

All of the genes having nucleotide sequences which encode these equivalents to the G protein-coupled receptor protein of the invention are included in the invention. Such various genes of the invention can also be produced by nucleic acid chemical synthesis methods in accordance with a usual method such as the phosphite triester method (Hunkapiller, M. et al. (1984), *Nature,* 10, 105–111), based on the information on the G protein-coupled receptor protein of the invention described in the foregoing. In this connection, codons for desired amino acid are well known, and they can be optionally selected and determined in the usual way, for example by taking codon usage of the host to be used into consideration (Crantham, R. et al. (1981), *Nucleic Acids Res.,* 9, r43–r74). In addition, partial modification of codons of these nucleotide sequences can be carried out in the usual way in accordance, for example, with the site specific mutagenesis (Mark, D. F. et al. (1984), *Proc. Natl. Acad. Sci. USA,* 81, 5662–5666) which uses a primer comprised of a synthetic oligonucleotide coding for the desired modification.

Determination of the sequence of DNA obtained by the above methods a) to d) can be carried out by, for example, the Maxam-Gilbert chemical modification method (Maxam, A. M. and Gilbert, E. (1980): "Methods in Enzymology", 65, 499–559) or the dideoxy nucleotide chain termination method (Messing, J. and Vieira, J. (1982), *Gene,* 19, 269–276) which uses M13.

Also, the vector of the invention, the host cell of the invention and the G protein-coupled receptor protein of the invention can be obtained by the following methods.

2) Production Method of Recombinant Protein of the G Protein-coupled Receptor of the Invention An isolated fragment containing a gene coding for the G protein-coupled receptor protein of the invention can transform other eucaryotic host cell by again integrating into an appropriate vector DNA. In addition, it is possible to express the gene in respective host cells by introducing an appropriate promoter and a sequence related to the gene expression into these vectors.

Cells of vertebrates, insects, yeast and the like are included in the eucaryotic host cells and, though not particularly limited, examples of commonly used vertebrate cells include COS cell which is a simian cell (Gluzman, Y. (1981), *Cell,* 23, 175–182), a dihydrofolate reductase deficient strain of Chinese hamster ovary cell (CHO) (Urlaub, G. and Chasin, L. A. (1980), *Proc. Natl. Acad. Sci. USA,* 77, 4216–4220), human fetal kidney HEK293 cell and 293-EBNA cell (Invitrogen) prepared by introducing Epstein Barr virus EBNA-1 gene into the human cell.

As the expression vector for vertebrate cells, a vector which contains a promoter positioned on the upstream of the gene to be expressed, an RNA splicing site, a polyadenylation site, transcription termination sequence and the like can generally be used, and it may further contain a replication origin as occasion demands. Examples of the expression vector include pSV2dhfr having SV40 early promoter (Subramani, S. et al. (1981), *Mol. Cell. Biol.,* 1, 854–864), pEF-BOS having human elongation factor promoter (Mizushima, S. and Nagata, S. (1990), *Nucleic Acids Res.,* 18, 5322), pCEP4 having cytomegalovirus promoter (Invitrogen) and the like, though not limited thereto.

In a case in which COS cell is used as the host cell, an expression vector which has SV40 replication origin, can perform autonomous growth in COS cell and has a transcription promoter, a transcription termination signal and an RNA splicing site can be used, and its examples include pME18S (Maruyama, K. and Takebe, Y. (1990), *Med. Immunol.,* 20, 27–32), pEF-BOS (Mizushima, S. and Nagata, S. (1990), *Nucleic Acids Res.,* 18, 5322), pCDM8 (Seed, B. (1987), *Nature,* 329, 840–842) and the like. The expression vector can be incorporated into COS cell by, for example, the DEAE-dextran method (Luthman, H. and Magnusson, G. (1983), *Nucleic Acids Res.,* 11, 1295–1308), the calcium phosphate-DNA co-precipitation method (Graham, F. L. and van der Ed., A. J. (1973), *Virology,* 52, 456–457), a method which uses FuGENE6™ (Boeringer Mannheim) or the electroporation method (Neumann, E. et al. (1982), *EMBO J.,* 1, 841–845), and a desired transformant cell can thus be obtained.

Also, when CHO cell is used as the host cell, a transformant cell capable of stably producing the novel G protein-coupled receptor protein can be obtained by carrying out co-transfection of an expression vector together with a vector capable of expressing neo gene which functions as a G418 resistance marker, such as pRSVneo (Sambrook, J. et al. (1989): "Molecular Cloning—A Laboratory Manual", Cold Spring Harbor Laboratory, NY) or pSV2-neo (Southern, P. J. and Berg, P. (1982), *J. Mol. Appl. Genet.,* 1, 327–341), and selecting a G418 resistant colony. In addition, when 293-EBNA cell is used as the host cell, a desired transformant cell can be obtained using an expression vector which has Epstein Barr virus replication origin and can perform autonomous growth in the 293-EBNA cell, such as pCEP4 (Invitrogen).

The thus obtained desired transformant can be cultured in the conventional way, and the G protein-coupled receptor protein of the invention is produced inside the cells or on the cell surface by this culturing. Regarding the medium to be used in this culturing, it can be optionally selected from various commonly used media depending on each host cell employed; for example, in the case of the COS cell, RPMI-1640 medium, Dulbecco's modified Eagle's minimum essential medium (DMEM) or the like can be used by adding serum components such as fetal bovine serum (FBS) and the like as occasion demands. Also, in the case of the 293-EBNA cell, Dulbecco's modified Eagle's minimum essential medium (DMEM) or the like medium supplemented with serum components such as fetal bovine serum (FBS) and the like can be used by further adding G418.

The G protein-coupled receptor protein of the invention thus produced inside the cell or on the cell surface of the transformant can be separated and purified therefrom by various known separation techniques making use of physical properties, chemical properties and the like of the receptor protein. Illustrative examples of such techniques, to be carried out after solubilization of the receptor protein-containing membrane fraction, include usual treatment with a protein precipitant, ultrafiltration, various liquid chromatography means such as molecular sieve chromatography (gel filtration), adsorption chromatography, ion exchange chromatography, affinity chromatography, high performance liquid chromatography (HPLC) and the like, dialysis and combinations thereof. In this connection, the membrane fraction can be obtained in the usual way. For example, it can be obtained by culturing the cells which expressed the G protein-coupled receptor protein on the surface, suspending them in a buffer and then homogenizing and centrifuging them. Also, when the G protein-coupled receptor protein is solubilized using a solubilizing agent as mild as possible (CHAPS, Triton® X-100, digitonin or the like), characteristics of the receptor can be maintained after the solubilization.

By effecting expression of the G protein-coupled receptor protein of the invention through its in-frame fusion with a marker sequence, confirmation of the expression the G protein-coupled receptor protein, confirmation of its intracellular localization, purification thereof and the like become possible. Examples of the marker sequence include FLAG® epitope, Hexa-Histidine tag, Hemagglutinin tag, myc epitope and the like. Also, when a specific sequence recognizable by a protease such as enterokinase, factor Xa or thrombin is inserted between a marker sequence and the G protein-coupled receptor protein, the marker sequence can be cut and removed by such a protease. For example, there is a report in which muscarinic acetylcholine receptor and Hexa-Histidine tag are connected with a thrombin-recognizing sequence (Hayashi, M. K. and Haga, T. (1996), *J. Biochem.,* 120, 1232–1238).

A method for the screening of compounds, peptides and antibodies capable of modifying activity of the G protein-coupled receptor protein is included in the invention. This screening method comprises adding an agent to be tested to a system in which an index of the modification of G protein-coupled receptor protein in response to a physiological characteristic of the G protein-coupled receptor protein is measured making use of the thus constructed G protein-coupled receptor protein, and measuring the index. The following screening methods can be cited as illustrative examples of this measuring system. Also, examples of useful drugs to be tested include compounds or peptides which are conventionally known to have G protein-coupled receptor ligand activity but their ability to selectively modify activity of the novel G protein-coupled receptor protein is not clear, known compounds and peptides registered in chemical files but their various G protein-coupled receptor ligand activities are unknown, compounds obtained by the method such as combinatorial chemistry techniques (Terrett, N. K. et al. (1995), *Tetrahedron,* 51, 8135–8137) and random peptides prepared by employing a phage display (Felici, F. et al. (1991), *J. Mol. Biol.,* 222, 301–310) or the like. In addition, culture supernatants of microorganisms, natural components originated from plants and marine organisms, animal tissue extracts and the like are also objects of the screening. Also useful are compounds or peptides obtained by chemically or biologically modifying a compound or peptide selected by the screening method of the invention.

3) Screening Methods of Ligands of the G Protein-coupled Receptor Protein of the Invention, Namely Compounds, Peptides and Antibodies which Modify Activity of the G Protein-coupled Receptor Protein of the Invention a) A Screening Method which Uses a Ligand Binding Assay Method Compounds, peptides and antibodies which bind to the G protein-coupled receptor protein of the invention (generally referred to as ligand) can be screened by a ligand binding assay method. A cell membrane sample obtained after expression of the receptor protein or a purified sample of the receptor protein is prepared, and a ligand purified for use in the ligand binding assay is radiation-labeled (50 to 2,000 Ci/mmol). Buffer solution, ions, pH and the like assay conditions are optimized, and the receptor protein-expressed cell membrane sample or the purified receptor protein sample is incubated in the thus optimized buffer for a predetermined period of time together with the radiation-labeled ligand. After the reaction, this is filtered through, e.g., a glass filter and washed with an appropriate amount of the buffer, and then the radioactivity remained on the filter (total binding amount) is measured using, e.g., a liquid scintillation counter. Nonspecific binding amount is measured by adding the unlabeled ligand in large excess in the reaction solution, and the specific binding amount is obtained by subtracting the nonspecific binding amount from the total binding amount. A ligand showing specific binding to the receptor protein-expressed cell membranes or the purified receptor protein can be selected as a ligand of the G protein-coupled receptor protein of the invention. In addition, a compound, peptide or antibody having agonist activity, or a compound, peptide or antibody having antagonist activity, of the G protein-coupled receptor protein can be screened making use of the binding inhibition of the thus obtained radioactive ligand as an index.

b) A Screening Method Which Uses a GTPγS Binding Method

Compounds, peptides and antibodies capable of modifying the activity of the G protein-coupled receptor protein of the invention can be screened by a GTPγS binding method (Lazareno, S. and Birdsall, N. J. M. (1993), *Br. J. Pharmacol.,* 109, 1120–1127). Cell membranes obtained after expression of the receptor protein is mixed with 400 pM of GTPγS labeled with $^{35}S$ in a solution of 20 mM HEPES (pH 7.4), 100 mM NaCl, 10 mM $MgCl_2$ and 50 mM GDP. After incubation in the presence or absence of an agent to be tested, this is filtered through, e.g., a glass filter and then radioactivity of the bound GTPγS is measured using, e.g., a liquid scintillation counter. A compound, peptide or antibody having agonist activity of the G protein-coupled receptor protein can be screened making use, as an index, of the increased specific GTPγS binding in the presence of the drug to be tested. Also, a compound, peptide or antibody having antagonist activity of the G protein-coupled receptor protein can be screened making use, as an index, of the suppression of increase in the GTPγS binding by the thus obtained compound, peptide or antibody having agonist activity.

c) A Screening Method Which Uses Changes in the Intracellular $Ca^{++}$ and cAMP concentrations Many G protein-coupled receptor proteins induce increase in $Ca^{++}$ and/or increase or decrease in cAMP concentration in the cells caused by an agonist stimulus. Accordingly, compounds, peptides and antibodies capable of modifying the activity of the G protein-coupled receptor protein of the invention can be screened making use of the changes in the intracellular $Ca^{++}$ or cAMP concentration. The $Ca^{++}$ concentration is measured using fura2 and the like, and the cAMP concentration is measured using a commercially available cAMP assay kit (by Amersham, etc.).

Alternatively, it is possible to measure the $Ca^{++}$ and cAMP concentrations indirectly, by detecting the transcription activity of a gene whose transcription amount is controlled depending on the $Ca^{++}$ and cAMP concentrations. A sample such as a compound, a peptide, a tissue extract or the like is allowed to react for a predetermined period of time with cells in which the receptor protein is expressed or host cells in which the receptor protein is not expressed (control cells), and the $Ca^{++}$ and cAMP concentrations are measured directly or indirectly. A compound, peptide or antibody having agonist activity can be screened making use, as an index, of the increase in $Ca^{++}$ and/or increase or decrease in cAMP concentration in the receptor protein-expressed cells by comparing with the control cells. Also, a compound, peptide or antibody having antagonist activity of the G protein-coupled receptor protein can be screened making use, as an index, of the increase in $Ca^{++}$ and/or increase or decrease in cAMP concentration caused by the thus obtained compound, peptide or antibody having agonist activity.

d) A Screening Method Which Uses Microphysiometer

Upon various signal responses of cells, trace amount of hydrogen ions outflow into the extracellular moiety is detected. Most of this outflow of hydrogen ions occur when metabolites formed by the fuel consumption of cells to obtain energy for their responses are increased or when signals of the cells are transmitted directly to the hydrogen ion pump. Since the G protein-coupled receptor protein of the invention requires energy for its signal transmission, outflow of hydrogen ions occurs when the receptor is activated. Since changes in pH caused by such a trace outflow of hydrogen ions in a medium around cells can be detected by CYTOSENSOR® Microphysiometer (Molecular Devices), it can be used for the detection of the activation energy consuming receptors.

A compound, a peptide, a tissue extract or the like is allowed to react for a predetermined period of time with cells in which the receptor protein is expressed or host cells in which the receptor protein is not expressed (control cells), and changes in the pH due to outflow of hydrogen ions are measured. A compound, peptide or antibody having agonist activity can be screened making use, as an index, of the changes in pH caused by the outflow of hydrogen ions from the receptor protein-expressed cells by comparing with the control cells. Also, a compound, peptide or antibody having antagonist activity of the G protein-coupled receptor protein can be screened making use, as an index, of the changes in pH due to the outflow of hydrogen ions caused by the thus obtained compound, peptide or antibody having agonist activity.

A medicament which contains as the active ingredient a compound, peptide or antibody capable of significantly modifying the activity of the G protein-coupled receptor protein or a G protein-coupled receptor protein selected by the screening method is included in the invention.

The antibody, such as a polyclonal antibody or monoclonal antibody, which reacts with the G protein-coupled receptor protein of the invention can be obtained by directly administering the novel G protein-coupled receptor protein or a fragment of the G protein-coupled receptor protein to various animals. It can also be obtained by a DNA vaccine method (Raz, E. et al. (1994), *Proc. Natl. Acad. Sci. USA,* 91, 9519–9523; Donnelly, J. J. et al. (1996), *J. Infect. Dis.,* 173, 314–320) using a plasmid in which a gene which encodes the G protein-coupled receptor protein of the invention is introduced.

The polyclonal antibody is produced from sera or eggs of an animal (e.g., rabbit, rat, goat, fowl or the like) immunized and sensitized by emulsifying the G protein-coupled receptor protein or a fragment thereof in an appropriate adjuvant such as complete Freund's adjuvant and administering it by intraperitoneal, subcutaneous or intravenous injection. The polyclonal antibody thus produced from sera or eggs can be separated and purified by the usual protein isolation purification methods. Examples of such methods include centrifugation, dialysis, salting out with ammonium sulfate, and chromatographic techniques using carriers such as DEAE-cellulose, hydroxyapatite, protein A agarose and the like.

An active antibody fragment containing a part of the antibody, such as F(ab')2, Fab, Fab' or Fv, can be obtained by digesting the thus separated and purified antibody with a proteolytic enzyme such as pepsin, papain or the like in the usual way and subsequently separating and purifying it by the usual protein isolation purification methods.

It is possible for those skilled in the art to easily produce a monoclonal antibody by the cell fusion method of Kohler and Milstein (Kohler, G. and Milstein, C. (1975), *Nature,* 256, 495–497).

Mice are immunized by intraperitoneal, subcutaneous or intravenous inoculation of an emulsion prepared by emulsifying the G protein-coupled receptor protein of the invention or a fragment thereof in an appropriate adjuvant such as complete Freund's adjuvant, several times repeatedly at intervals of several weeks. After final immunization, spleen cells are collected and fused with myeloma cells to prepare a hybridoma.

Myeloma cells having hypoxanthine-guanine phosphoribosyltransferase deficiency, thymidine kinase deficiency or the like marker, such as mouse myeloma cell strain P3X63Ag8.U1, are used as the myeloma cells for obtaining the hybridoma. Also, polyethylene glycol is used as the fusing agent. In addition, Eagle's minimum essential medium, Dulbecco's modified minimum essential medium, RPMI-1640 or the like generally used medium is optionally supplemented with 10 to 30% of fetal bovine serum and used as the medium for the preparation of the hybridoma. Fused strains are selected by the HAT selection method. Screening of hybridoma is carried out using a conventional method such as the culture supernatant by ELISA, immunohistological staining or the like or by the screening method described in the foregoing, and a hybridoma clone secreting the antibody of interest is selected. Also, monoclonal nature of the hybridoma is confirmed by repeating subcloning by means of limiting dilution analysis. When the thus obtained hybridoma is cultured for 2 to 4 days in a medium or for 10 to 20 days in the abdominal cavity of a BALB/c mice pretreated with pristane, the antibody in an amount sufficient for purification is produced.

The thus produced monoclonal antibody can be separated and purified from the culture supernatant or ascites by the usual protein isolation purification methods. Examples of such methods include centrifugation, dialysis, salting out with ammonium sulfate, and chromatographic techniques using carriers such as DEAE-cellulose, hydroxyapatite, protein A agarose and the like. In addition, the monoclonal antibody or an antibody fragment containing a part thereof can also be produced by integrating entire portion or a part of a gene coding for the antibody into an expression vector and introducing into *Escherichia coli,* yeast or animal cells. An active antibody fragment containing a part of the antibody, such as F(ab')2, Fab, Fab' or Fv, can be obtained by digesting the thus separated and purified antibody with a proteolytic enzyme such as pepsin, papain or the like in the usual way and subsequently separating and purifying it by the usual protein isolation purification methods.

In addition, it is possible to obtain an antibody capable of reacting with the G protein-coupled receptor protein of the invention as single chain Fv or Fab by the method of Clackson et al. or Zebedee et al. (Clackson, T. et al. (1991), *Nature,* 352, 624–628; Zebedee, S. et al. (1992), *Proc. Natl. Acad. Sci. USA,* 89, 3175–3179). It is also possible to obtain a human antibody by immunizing a transgenic mouse in which a mouse antibody gene is replaced by a human antibody gene (Lonberg, N. et al. (1994), *Nature,* 368, 856–859).

The medicament of the invention is characterized in that it has a novel pharmacological action to selectively control activity of the G protein-coupled receptor, and examples of the use of the medicament include central nervous system diseases which are induced by abnormalities of the G protein-coupled receptor activity (acceleration, reduction, denaturation and the like) or which express the abnormalities as complications.

The pharmaceutical preparation which contains a compound, peptide, antibody or antibody fragment capable of modifying activity of the G protein-coupled receptor protein of the invention, as the active ingredient, can be prepared using carriers, fillers and other additives generally used in the preparation of medicaments, in response to each type of the active ingredient.

Examples of its administration include oral administration in the form of tablets, pills, capsules, granules, fine granules, powders, oral solutions and the like, and parenteral administration in the form of intravenous, intramuscular and the like injections, suppositories, percutaneous preparations, transmucosal absorption preparations and the like. Particularly, in the case of peptides which are digested in the stomach, intravenous injection or the like parenteral administration is desirable.

In the solid composition for use in the oral administration according to the present invention, one or more active substances are mixed with at least one inert diluent such as lactose, mannitol, glucose, microcrystalline cellulose, hydroxypropylcellulose, starch, polyvinyl pyrrolidone or aluminum magnesium metasilicate. In the usual way, the composition may contain additives other than the inert diluent, for example, a lubricant, a disintegrating agent, a stabilizing agent and a solubilizing or solubilization assisting agent. If necessary, tablets or pills may be coated with a sugar coating or a film of a gastric or enteric substance.

The liquid composition for oral administration includes emulsions, solutions, suspensions, syrups and elixirs and contains a generally used inert diluent such as purified water or ethanol. In addition to the inert diluent, this composition may also contain other additives such as moistening agents, suspending agents, sweeteners, flavors and antiseptics.

The injections for parenteral administration includes aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oils (e.g., olive oil), alcohols (e.g., ethanol), polysorbate 80 and the like. Such a composition may further contain a moistening agent, an emulsifying agent, a dispersing agent, a stabilizing agent, a solubilizing or solubilization assisting agent, an antiseptic and the like. These compositions are sterilized for example by filtration through a bacteria retaining filter, blending of a germicide or irradiation. Alternatively, they may be used by firstly making into sterile solid compositions and dissolving them in sterile water or other sterile solvent for injection use prior to their use.

The dose is optionally decided by taking into consideration strength of each active ingredient selected by the screening method described in the foregoing and symptoms, age, sex and the like of each patient to be administered.

BRIEF DESCRIPTION OF THE DRAWINGS

FIG. 1 shows alignment of amino acid sequences of SREB1, SREB2 and SREB3.

FIG. 2 shows a result of Northern analysis of SREB1 in human organs.

FIG. 3 shows a result of Northern analysis of SREB1 in each region of human brain.

FIG. 5 shows a result of Northern analysis of SREB2 in each region of human brain.

FIG. 7 shows a result of Northern analysis of SREB3 in each region of human brain.

BEST MODE FOR CARRYING OUT THE INVENTION

Figure 4:
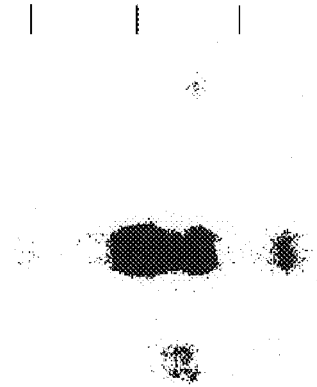
FIG. 4 shows a result of Northern analysis of SREB2 in human organs.

In order to disclose the invention further illustratively, Examples are described in the following, but the invention is not limited to these Examples. In this connection, unless otherwise noted, they can be carried out in accordance with known methods (Maniatis, T. et al. (1982): "Molecular Cloning—A Laboratory Manual", Cold Spring Harbor Laboratory, NY).

EXAMPLE 1

Isolation of Genes Coding for the Novel G Protein-coupled Receptor Family Proteins Full length cDNA coding for the G protein-coupled receptor family protein (SREB1, SREB2 or SREB3) of the invention was obtained by RT-PCR using human brain origin poly $A^+$ RNA (Clontech) as the template.

In the amplification of the novel G protein-coupled receptor human SREB1, 5'-AAAATCTAGA CGCGATGGCGAACGCGAGCGA-3' (SEQ ID NO: 7) was used as the forward primer, and 5'-AAAATCTAGA GTCTATGTGGCGGGGCCTCCC-3' (SEQ ID NO: 8) as the reverse primer (XbaI site is added to each 5' terminus). RT-PCR was carried out using Pfu DNA polymerase (Stratagene) and by repeating a cycle of 98° C. (20 seconds)/64° C. (30 seconds)/74° C. (3 minutes) 34 times in the presence of 5% formamide. As the result, a DNA fragment of about 1.2 kbp was amplified. This fragment was digested with XbaI and then cloned using pCEP4 plasmid (Invitrogen). Since the pCEP4 plasmid contains CMV promoter which shows strong promoter activity in animal cells, it can be used in expressing recombinant proteins in animal cells. Nucleotide sequence of the thus obtained clone was analyzed by the dideoxy terminator method using ABI377 DNA Sequencer (Applied Biosystems). The thus revealed sequence is shown in SEQ ID NO: 1 of the Sequence Listing.

This sequence contains an open reading frame of 1,125 bases (from the 1st position to the 1125th position of SEQ ID NO: 1). An amino acid sequence (375 amino acids) deduced from the open reading frame is shown in SEQ ID NO: 2 of the Sequence Listing. Since the deduced amino acid sequence contains seven hydrophobic regions considered to be the transmembrane domains which is a characteristic of the G protein-coupled receptor, it was found that this gene encodes the G protein-coupled receptor.

In the amplification of the novel G protein-coupled receptor human SREB2, 5'-AAAATCTAGA TCTATGGCGAACTATAGCCATGCA-3' (SEQ ID NO: 9) was used as the forward primer, and 5'-AAAATCTAGA AAGGCTAAAGATTTACAGATGCTCC-3' (SEQ ID NO: 10) as the reverse primer (XbaI site is added to each 5' terminus). RT-PCR was carried out using Pfu DNA polymerase (Stratagene) and by repeating a cycle of 96° C. (20 seconds)/54° C. (30 seconds)/74° C. (3 minutes) 34 times. As the result, a DNA fragment of about 1.2 kbp was amplified. This fragment was digested with XbaI and then cloned using pCEP4 plasmid (Invitrogen). Nucleotide sequence of the thus obtained clone was analyzed by the dideoxy terminator method using ABI377 DNA Sequencer (Applied Biosystems). The thus revealed sequence is shown in SEQ ID NO: 3 of the Sequence Listing.

This sequence contains an open reading frame of 1,110 bases (from the 1st position to the 1110th position of SEQ ID NO: 3). An amino acid sequence (370 amino acids) deduced from the open reading frame is shown in SEQ ID NO: 4 of the Sequence Listing. Since the deduced amino acid sequence contains seven hydrophobic regions considered to be the transmembrane domains which is a characteristic of the G protein-coupled receptor, it was found that this gene encodes the G protein-coupled receptor.

In the amplification of the novel G protein-coupled receptor human SREB3, 5'-AAAATCTAGA GTATGGCCAACACTACCGGAGAG-3' (SEQ ID NO: 11) was used as the forward primer, and 5'-AAAATCTAGA CCTGTCTGCCTACCAGCCTGC-3' (SEQ ID NO: 12) as the reverse primer (XbaI site is added to each 5' terminus). RT-PCR was carried out using Pfu DNA polymerase (Stratagene) and by repeating a cycle of 98° C. (20 seconds)/62° C. (30 seconds)/74° C. (3 minutes) 34 times in the presence of 5% formamide. As the result, a DNA fragment of about 1.2 kbp was amplified. This fragment was digested with XbaI and then cloned using pCEP4 plasmid (Invitrogen). Nucleotide sequence of the thus obtained clone was analyzed by the dideoxy terminator method using ABI377 DNA Sequencer (Applied Biosystems). The thus revealed sequence is shown in SEQ ID NO: 5 of the Sequence Listing.

This sequence contains an open reading frame of 1,119 bases (from the 1st position to the 1119th position of SEQ ID NO: 5). An amino acid sequence (373 amino acids) deduced from the open reading frame is shown in SEQ ID NO: 6 of the Sequence Listing. Since the deduced amino acid sequence contains seven hydrophobic regions considered to be the transmembrane domains which is a characteristic of the G protein-coupled receptor, it was found that this gene encodes the G protein-coupled receptor.

Homology of the novel G protein-coupled receptor SREB family (SREB1, SREB2 or SREB3) with a known G protein-coupled receptor family is 25% or less, respectively.

On the other hand, homology of SREB1 with SREB2 is 52%, homology of SREB1 with SREB3 is 52% and homology of SREB2 with SREB3 is 63%, which are significantly higher than the homology with known G protein-coupled receptors (FIG. 1). This fact shows that the G protein-coupled receptors SREB1, SREB2 and SREB3 of the invention form a novel G protein-coupled receptor family independent of the known G protein-coupled receptors.

EXAMPLE 2

Expression Distribution of Human Novel G Protein-coupled Receptor Family Genes in Tissues Expression distribution of the G protein-coupled receptor genes of the invention was analyzed by the northern blot hybridization method. A cDNA fragment (from the 722nd position to the 1054th position in SEQ ID NO: 1) was used as the probe of human SREB1. Poly $A^+$ RNA (2 $\mu$g) originated from each of human organs was blotted on a membrane (Clontech), and its hybridization with the probe was carried out at 42° C. (18 hours) in a solution containing 50% formamide, 5×SSPE, 10× Denhardt's solution, 2% SDS and 100 $\mu$g/ml denatured salmon sperm DNA. The membrane was finally washed twice (65° C. for 30 minutes) with a solution containing 0.2×SSC and 0.1% SDS. As shown in FIG. 2, when the northern analysis was carried out on each of human organs (heart, brain, placenta, lung, liver, skeletal muscle, kidney, pancreas, spleen, thymus, prostate, testis, ovary, small intestine, large intestine and peripheral leukocyte), 3 kb of mRNA was detected in the brain, ovary, testis, heart and prostate, and 3 kb and 2.3 kb mRNA in the peripheral leukocyte. Also, a signal of 3 kb was slightly detected in the pancreas, too. In addition, the northern analysis was also carried out on each of the regions of the human brain (amygdala, caudate nucleus, corpus callosum, hippocampus, substania nigra, subthalamic nucleus, thalamus, cerebellum, cerebral cortex, medulla, spinal cord, occipital lobe, frontal lobe, temporal lobe and putamen). Since the 3 kb mRNA of the G protein-coupled receptor human SREB1 gene of the invention was detected in all of the examined human brain regions, it was found that it is expressed broadly in the human brain (FIG. 3).

A cDNA fragment (from the 558th position to the 888th position in SEQ ID NO: 3) was used as the probe of human SREB2. When the northern analysis was carried out under the same conditions, 3.2 kb mRNA was detected in the brain, and 2.4 kb, 3.5 kb and 6.3 kb mRNA in the testis, as shown in FIG. 4. Also, the signal of 3.5 kb was detected in the placenta and spleen, and the signal of 3.2 kb in small intestine, all slightly. Among regions in the brain, the 3.2 kb mRNA of the G protein-coupled receptor human SREB2 gene of the invention was abundantly detected in the amygdala, caudate nucleus, hippocampus, substania nigra, subthalamic nucleus, thalamus, cerebellum, cerebral cortexes and putamen, but not so much in the corpus callosum, medulla and spinal cord. In addition, a signal of 7.8 kb was slightly detected in each of the grain regions (FIG. 5)

Figure 6:
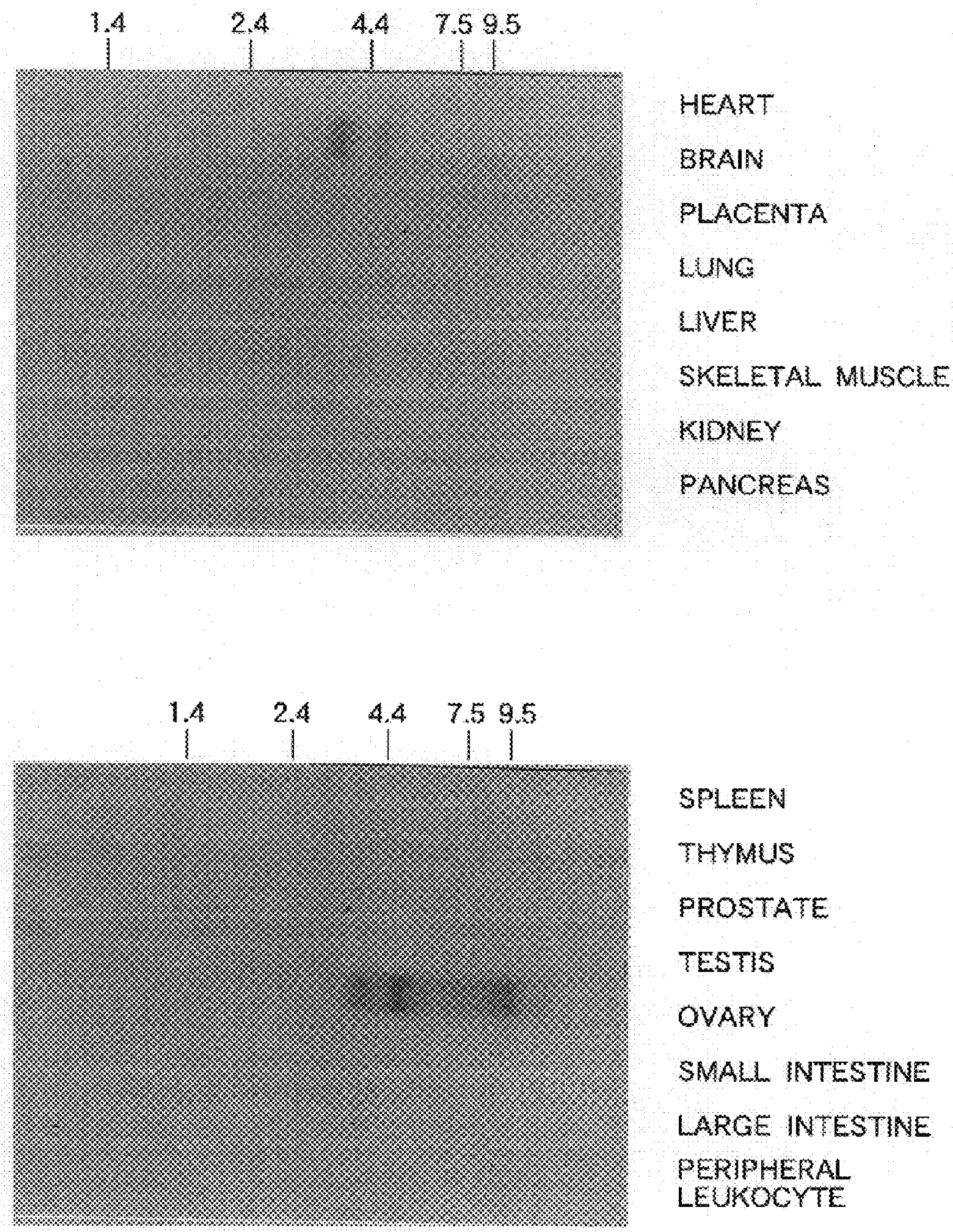
FIG. 6 shows a result of Northern analysis of SREB3 in human organs.

A cDNA fragment (from the 1st position to the 652nd position in SEQ ID NO: 5) was used as the probe of human SREB3. When the northern analysis was carried out under the same conditions, 4 kb and 5.1 kb mRNA was detected in the brain, and 4 kb, 5.1 kb and 9.7 kb mRNA in the ovary, as shown in FIG. 6. The G protein-coupled receptor human SREB3 gene of the invention was detected in each region of the brain as signals of mainly 4 kb, 5.1 kb and slightly 9.7 kb, and the 4 kb mRNA was detected in the amygdala, hippocampus, subthalamic nucleus, cerebellum and cerebral cortex, and the 5.1 kb mRNA in the substania nigra, subthalamic nucleus and spinal cord, relatively abundantly (FIG. 7).

The above results showed that the G protein-coupled receptor family genes SREB1, SREB2 and SREB3 of the invention are expressed mainly in the central nervous system and urinary organ/reproductive organ system.

EXAMPLE 3

Confirmation of the Expression of the Novel Human G Protein-coupled Receptor Family Proteins pCEP4 (Invitrogen) was used as the expression vector for expressing human SREB1, SREB2 or SREB3. In this case, in order to fuse a FLAG® epitope as a marker sequence with the N terminus of human SREB1, SREB2 or SREB3, ATGGACTACAAGGACGACGATGA-CAAGGGGATCCTG (SEQ ID NO: 13) was inserted into the 5' terminus of the protein coding sequence of SREB1, SREB2 or SREB3. The thus constructed plasmids were named pCEP4-FL-SREB1, pCEP4-FL-SREB2 and pCEP4-FL-SREB3, respectively. By the use of these plasmids, a polypeptide in which a sequence Met Asp Tyr Lys Asp Asp Asp Asp Lys Gly Ile Leu (SEQ ID NO: 14) is fused with the N terminus of the polypeptide of SREB1, SREB2 or SREB3 is expressed.

Figure 8:
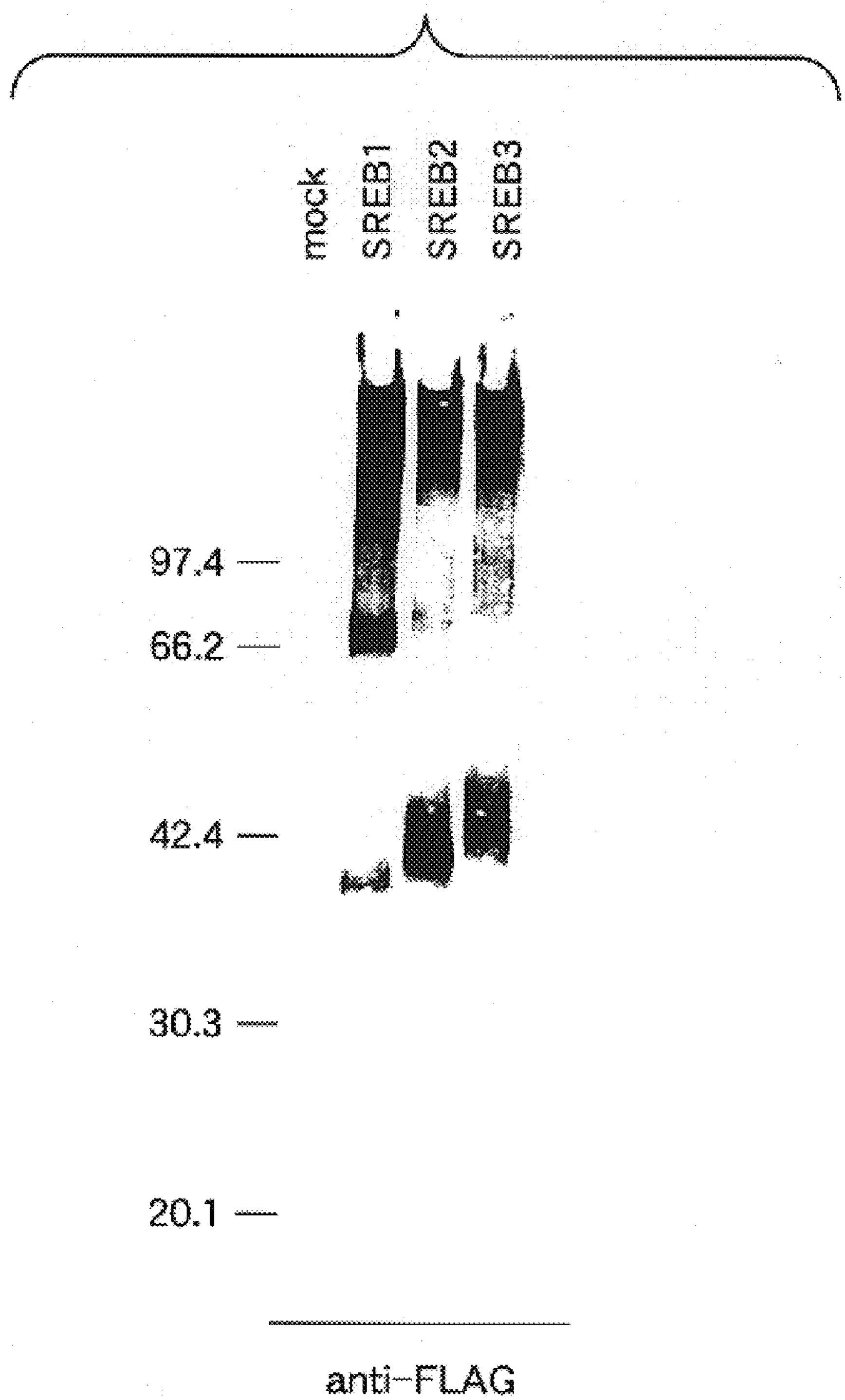
FIG. 8 shows a result confirming expression of SREB1, SREB2 or SREB3 protein.

A $1\times10^6$ cells portion of 293-EBNA (Invitrogen) was inoculated into a 10 cm Petri dish and cultured for 1 day, and then gene transfer of 8 $\mu$g of pCEP4-FL-SREB1, pCEP4-FL-SREB2, pCEP4-FL-SREB3 or pCEP4-FL (vector alone) was carried out using FuGENE6™ (Boeringer Mannheim). After the gene transfer, the cells were cultured for 1 day, harvested, washed, suspended in 20 mM of Tris-HCl (pH 7.4)/150 mM NaCl/Complete™ (Boeringer Mannheim) and then homogenized using Polytron. The homogenate was mixed with Triton® X-100, Digitonin and sodium cholate to final concentrations of 0.2%, 0.1% and 0.2% and then solubilized by incubating at 4° C. for 2 hours. Immunoprecipitation of the FLAG® epitope fusion protein from the thus solubilized sample was effected using M2-agarose (Sigma). The immune precipitate was eluted with 200 $\mu$M FLAG® peptide/20 mM Tris-HCl (pH 7.4)/150 mM NaCl. The eluted sample was concentrated, subjected to electrophoresis using SDS/10%-20% acrylamide gel (Daiichi Pure Chemicals) and then transferred on a PVDF membrane using a blotting apparatus. The PVDF membrane after the transfer was subjected to blocking and then allowed to react with a mouse anti-FLAG® monoclonal antibody (M2; Sigma) and a horseradish peroxidase-labeled rabbit anti-mouse IgG polyclonal antibody (Zymed) in that order. After the reaction, expression of SREB1, SREB2 or SREB3 protein was confirmed using ECL™ Western Blotting Detection System (Amersham-Pharmacia) (FIG. 8).

The protein capable of reacting with the anti-FLAG® antibody was not present in the cells in which pCEP4-FL was introduced but detected in the cells in which pCEP4-FL-SREB1, pCEP4-FL-SREB2 or pCEP4-FL-SREB3 was introduced as a band of 35 to 45 kDa. Estimated molecular weights of human SREB1, human SREB2 and human SREB3 were 39.8 kDa, 42.0 kDa and 41.5 kDa, respectively, and their bands were found at positions of almost expected molecular weights. In addition, a band of 65 to 75 kDa considered to be a dimer was detected in the case of human SREB1.

EXAMPLE 4

Isolation of Gene Coding for Rat SREB1 (rSREB1), Rat SREB2 (rSREB2) or Rat SREB3 (rSREB3) Protein Complete length cDNA coding for rSREB2, rSREB2 or rSREB3 was obtained by RT-PCR using rat brain origin poly $A^+$ RNA (Clontech) as the template.

In the amplification of rSREB1, 5'-AAAATCTAGACGGCGATGGCGAACGCTAGTGA-3' (SEQ ID NO: 15) was used as the forward primer, and 5'-AAAATCTAGA CACTTTGAGAGTCTTGTGAAGGC-3' (SEQ ID NO: 16) as the reverse primer (XbaI site is added to each 5' terminus). Amplification, cloning and nucleotide sequence determination of cDNA were carried out by the same methods of Example 1. The thus revealed sequence is shown in SEQ ID NO: 21 of the Sequence Listing.

This sequence contains an open reading frame of 1,131 bases (from the 1st position to the 1131st position of SEQ ID NO: 21). An amino acid sequence (377 amino acids) deduced from the open reading frame is shown in SEQ ID NO: 22 of the Sequence Listing. Since the deduced amino acid sequence coincided in 97% frequency with the human SREB1, it was found that this gene encodes rSREB1.

In the amplification of rSREB2, 5'-AAAATCTAGATCTATGGCGAACTATAGCCATGC-3' (SEQ ID NO: 17) was used as the forward primer, and 5'-AAAATCTAGA AAGGCTAAAGATTTACAGATGCTCC-3' (SEQ ID NO: 18) as the reverse primer (XbaI site is added to each 5' terminus). Amplification, cloning and nucleotide sequence determination of cDNA were carried out by the same methods of Example 1. The thus revealed sequence is shown in SEQ ID NO: 23 of the Sequence Listing.

This sequence contains an open reading frame of 1,110 bases (from the 1st position to the 1110th position of SEQ ID NO: 23). An amino acid sequence (370 amino acids) deduced from the open reading frame is shown in SEQ ID NO: 24 of the Sequence Listing. Since the deduced amino acid sequence coincided in 100% frequency with the human SREB2, it was found that this gene encodes rSREB2.

In the amplification of rSREB3, 5'-AAAATCTAGACAAATACTGAACTGGCCGATCCCC-3' (SEQ ID NO: 19) was used as the forward primer, and 5'-AAAATCTAGA TGTTGGCCCCAGTATGGTGATCAT-3' (SEQ ID NO: 20) as the reverse primer (XbaI site is added to each 5' terminus). Amplification, cloning and nucleotide sequence determination of cDNA were carried out by the same methods of Example 1. The thus revealed sequence is shown in SEQ ID NO: 25 of the Sequence Listing.

This sequence contains an open reading frame of 1,119 bases (from the 1st position to the 1119th position of SEQ ID NO: 25). An amino acid sequence (373 amino acids) deduced from the open reading frame is shown in SEQ ID NO: 26 of the Sequence Listing. Since the deduced amino acid sequence coincided in 99% frequency with the human SREB3, it was found that this gene encodes rSREB3.

EXAMPLE 5

Preparation of Antibody for Human SREB1

A partial amino acid sequence of human SREB1 was fused with glutathione-S-transferase (GST) and used as the immunization antigen for the preparation of antibody for human SREB1. Illustratively, a cDNA fragment corresponding to a region of from the 208th position to the 282nd position (3LO) and a region of from the 351st position to the 375th position (C24) of the human SREB1 amino acid sequence (SEQ ID NO: 2) was amplified by PCR in an way to bind cleavage sites of restriction enzymes BamHI and XhoI, and inserted between BamHI and XhoI sites of GST Gene Fusion Vector (pGEX-5X-1: Amersham-Pharmacia). Competent cells of an *Escherichia coli* strain BL21(DE3) pLysS (Novagen) were transformed with the thus constructed plasmid. By culturing the transformant and inducing expression of the gene with 1 mM IPTG, a GST-3LO fusion protein and a GST-C24 fusion protein were expressed in the *E. coli* cells. The GST-3LO and GST-C24 were purified from disrupted *E. coli* cells using Glutathione Sepharose 4B (Amersham-Pharmacia) in accordance with the instruction attached thereto.

The thus purified GST-3LO fusion protein was mixed with the same amount of Freund's complete adjuvant (CalBioChem) and emulsified, and the emulsion was administered to a female white Leghorn (140 days of age) at around the bursa of Fabricius. The initial dose was 1 mg, and it was administered thereafter in 0.5 mg portions 4 times at intervals of 2 weeks. After the final immunization, eggs were collected, the yolk of eggs was diluted with physiological saline and defatted using dextran sulfate, and then IgY was purified using DEAE Sepharose® (Amersham-Pharmacia) to obtain anti-3LO antibody. Also, the purified GST-C24 fusion protein was mixed with the same amount of TiterMax® Gold (CytRX) and emulsified, and the emulsion was administered under the dorsal skin of a Japanese white rabbit (6 weeks of age). Its initial dose was 1 mg, and it was administered thereafter in 0.5 mg portions 2 times at intervals of 2 weeks. After the final immunization, blood was collected, and IgG was purified from the serum using Protein G Sepharose® (Amersham-Pharmacia) in accordance with the instruction attached thereto, thereby obtaining anti-C24 antibody.

Since the anti-3LO antibody uses a region of from the 208th position to the 282nd position of the human SREB1 amino acid sequence (SEQ ID NO: 2) as the antigen and this partial amino acid sequence contains a large number of sequences common to SREB1, SREB2 and SREB3 (cf. FIG. 1), there is a possibility that the anti-3LO antibody commonly recognizes SREB1, SREB2 and SREB3. Also, since the anti-C24 antibody uses a region of from the 351st position to the 375th position of the human SREB1 amino acid sequence (SEQ ID NO: 2) as the antigen and this partial amino acid sequence is a sequence in which SREB2 and 3 are not present but SREB1 alone is present (cf. FIG. 1), there is a possibility that the anti-C24 antibody recognizes only SREB1. In consequence, in order to confirm the specificity of anti-3LO antibody and anti-C24 antibody, Western blotting was carried out using the immune precipitate of anti-FLAG® antibody of 293-EBNA in which SREB1, SREB2 or SREB3 was expressed, prepared in Example 3, and the anti-3LO antibody and anti-C24 antibody.

Figure 9:
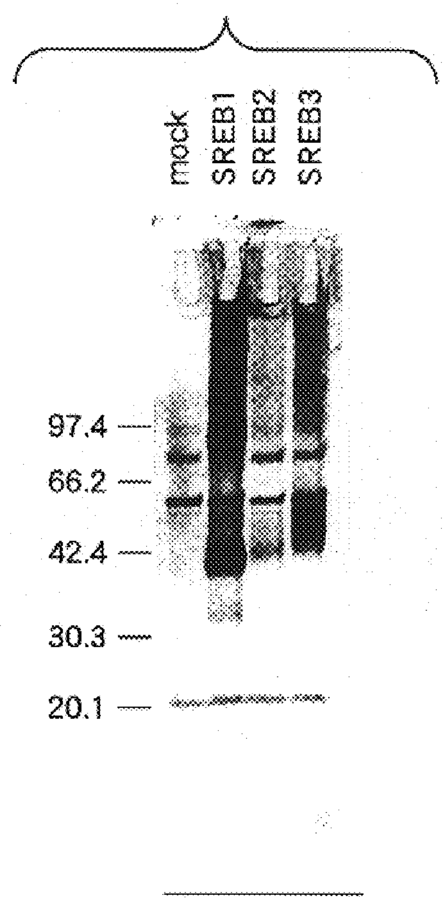
FIG. 9 shows binding activity of anti-3LO antibody for SREB1, SREB2 or SREB3.
Figure 10:
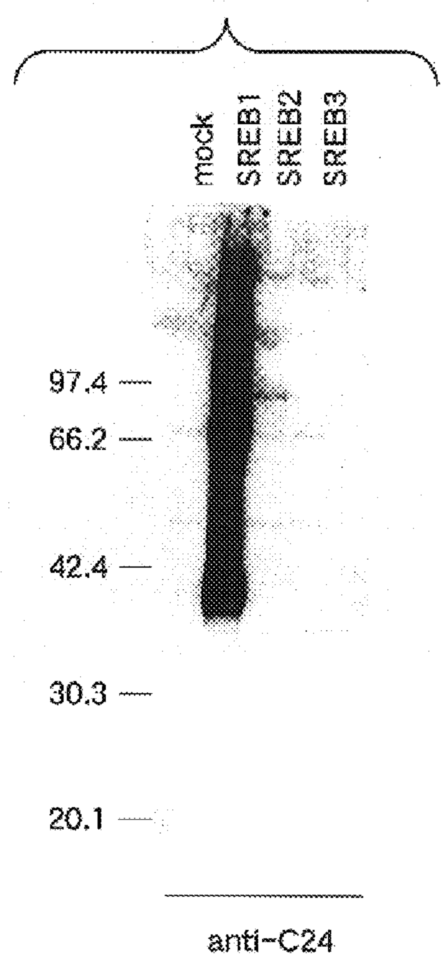
FIG. 10 shows binding activity of anti-C24 antibody for SREB1.

Illustratively, each sample was subjected to electrophoresis using SDS/10%-20% acrylamide gel (Daiichi Pure Chemicals) and then transferred on a PVDF membrane using a blotting apparatus. The PVDF membrane after the transfer was subjected to blocking and then allowed to react with 10 μg/ml of the anti-3LO antibody and a horseradish peroxidase-labeled rabbit anti-chicken IgG polyclonal antibody (Zymed) in that order or with 10 μg/ml of the anti-C24 antibody and a horseradish peroxidase-labeled goat anti-rabbit IgG polyclonal antibody (MBL) in that order. After the reaction, color development was carried out using ECL™ Western Blotting Detection System (Amersham-Pharmacia). A band reacting with the anti-3LO antibody was detected at the same position of the anti-FLAG® antibody of Example 3 in cells in which pCEP4-FL-SREB1, pCEP4-FL-SREB2 or pCEP4-FL-SREB3 (FIG. 9) was introduced. Also, a band reacting with the anti-C24 antibody was detected at the same position of the anti-FLAG® antibody of Example 3 only in the cells in which pCEP4-FL-SREB1 was introduced (FIG. 10).

Based on the above results, it was confirmed that the anti-3LO antibody is an antibody which recognizes SREB1, SREB2 or SREB3, and the anti-C24 antibody is an antibody which recognizes only SREB1. The use of these antibodies has rendered possible the detection of natural SREB1, SREB2 or SREB3 by the method such as the Western blotting, immunohistological staining or the like.

EXAMPLE 6

Evaluation of Transcription Activity via cAMP-response Element (CRE) or Serum Response Element (SRE) in Human SREB1-, SREB2- or SREB3-introduced Cells Increase in the transcription activity mediated by CRE or SRE is induced by the activation of the intracellular information transmission system of various G protein-coupled receptors (Lolait, S. J. et al. (1992), *Nature,* 357, 336–339; Hoeltzel, W. L. et al. (1997), *Am. J. Physiol.,* 273, C2037–C2045; An, S. et al. (1998), *J. Biol. Chem.,* 273, 7906–7910). Also, it is known that the intracellular information transmission system of G protein-coupled receptors is partially activated via a certain transitional active conformation even in the absence of agonist (Kenakin, T. (1995), *Trens. Pharmacol. Sci.,* 16, 188–192). Accordingly, if changes in the CRE- or SRE-mediated transcription activity in SREB1-, SREB2- or SREB3-introduced cells are found even in the absence of agonist, it can be confirmed that the G protein-coupled receptor is functional and that activation of the G protein-coupled receptor intracellular information transmission system leads to the CRE- and SRE-mediated transcription activity.

Using pEF-BOS (Mizushima, S. and Nagata, S. (1990), *Nucleic Acids Res.,* 18, 5322) as the expression vector for expressing human SREB1, SREB2 or SREB3, pEF-BOS-SREB1, pEF-BOS-SREB2 and pEF-BOS-SREB3 were prepared. A $8\times10^4$ cells portion of 293-EBNA (Invitrogen) was inoculated into a 24-well plate and cultured for 1 day, and then gene transfer of 250 ng of pEF-BOS-SREB1, pEF-BOS-SREB2, pEF-BOS-SREB3 or pEF-BOS (vector alone) was carried out together with 25 ng of a CRE-reporter plasmid pCRE-Luc (Stratagene) or an SRE-reporter plasmid pSRE-Luc (Stratagene), using FuGENE6™ (Boeringer Mannheim) (3 wells for each). After the gene transfer, the cells were lysed at every 12 hours using PicaGene® Cell Culture Lysis Reagent Luc (Nippon Gene), and the activity of luciferase produced from each reporter plasmid was measured using PicaGene® Luminescence Kit (Nippon Gene).

Figure 11:
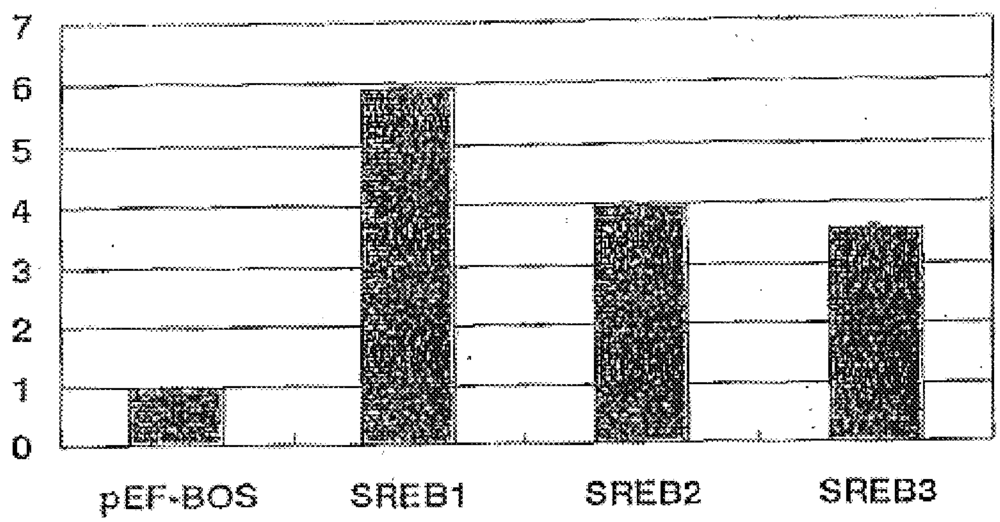
FIG. 11 shows pCRE-Luc derived luciferase activity in cells in which SREB1, SREB2 or SREB3 was introduced.
Figure 12:
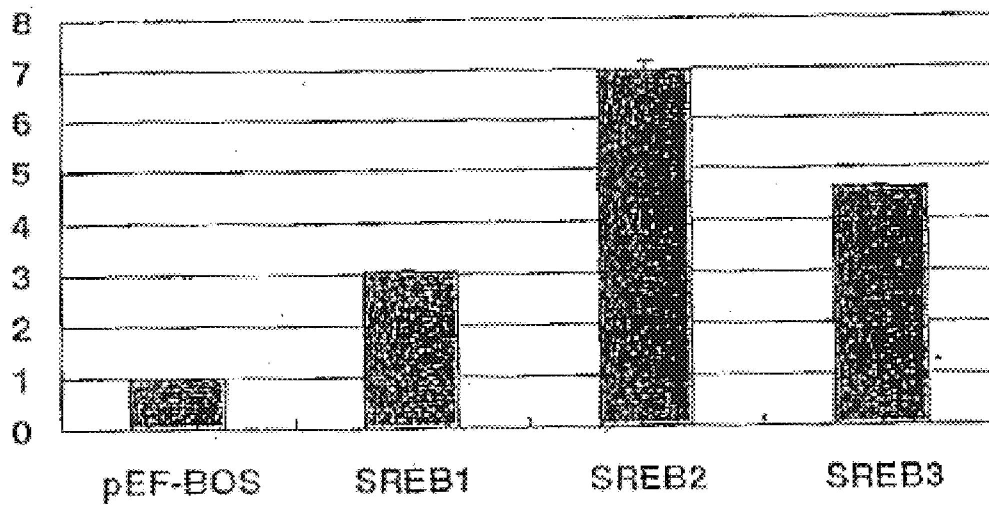
FIG. 12 shows pSRE-Luc derived luciferase activity in cells in which SREB1, SREB2 or SREB3 was introduced.

The luciferase activity in the SREB1-, SREB2- or SREB3-introduced cells after 24 hours of the gene transfer was treated as a relative activity to the luciferase activity of the vector alone introduced cells (control) (the control was defined as 1), with the results shown in FIG. 11 (pCRE-Luc derived luciferase activity) and FIG. 12 (pSRE-Luc derived luciferase activity). The CRE-mediated transcription activity increased most sharply in the SREB1-introduced cells and also increased significantly in the SREB2- and SREB3-introduced cells in comparison with the control. On the other hand, the SRE-mediated transcription activity increased most sharply in the SREB2-introduced cells and also increased significantly in the SREB1- and SREB3-introduced cells in comparison with the control.

It was revealed by these results that the SREB1, SREB2 and SREB3 are functional receptors, and activation of the intracellular information transmission system of these G protein-coupled receptors leads to the increase in the CRE- or SRE-mediated transcription activity.

Industrial Applicability

Novel G protein-coupled receptor family proteins SREB1, SREB2 and SREB3 expressing in the central nervous system, genes coding for these proteins, vectors containing these genes, host cells containing these vectors and methods for producing these G protein-coupled receptor proteins were provided by the present invention.

Also, it rendered possible to screen new medicaments, particularly new therapeutic agents for central nervous system diseases, through the screening of compounds, peptides and antibodies capable of modifying activities of the G protein-coupled receptor proteins of the invention by allowing the G protein-coupled receptors to contact with drugs to be tested.

Regarding the medicament of the invention which contains, as the active ingredient, a compound, peptide or antibody capable of specifically modifying activity of the G protein-coupled receptor proteins expressing in the central nervous system, its usefulness as therapeutic agents and the like for functional/organic diseases of the central nervous system. Also, since the G protein-coupled receptor family proteins of the invention are expressed not only in the central nervous system but also in the urinary organ/reproductive organ system, usefulness as therapeutic drugs and the like for diseases related to the urinary organ/reproductive organ system can be expected from the medicament which contains, as the active ingredient, a compound, peptide or antibody capable of specifically modifying their activities. In addition, since a member of the G protein-coupled receptors of the invention, such as SREB1 protein, is expressed not only in the central nervous system and urinary organ/reproductive organ system but also in the heart and peripheral leukocytes, a medicament which contains, as the active ingredient, a compound, peptide or antibody capable of specifically modifying the activity of SREB1 protein can be expected for its usefulness as therapeutic drugs and the like for circulatory system diseases and immune inflammation system diseases, in addition to central diseases and diseases related to the urinary organ/reproductive organ system.

The novel G protein-coupled receptor family SREB1, SREB2 or SREB3 of the invention has markedly high conservation ratio of amino acids in human and rat. This conservation ratio is most highest among the existing G protein-coupled receptor families, which seems to show that the novel G protein-coupled receptor family of SREB1, SREB2 and SREB3 is taking important roles in the living body, particularly a physiological role in the central nervous system. Also, since their amino acid sequences have a conversation ratio of 97% or more in human and rat, it is considered that almost no interspecies differences are present regarding activities of drugs which act upon the novel G protein-coupled receptor family SREB1, SREB2 or SREB3. In consequence, when the G protein-coupled receptor protein of the invention itself or a compound or protein obtained by a screening using the receptor is developed as a medicament, the receptor has an advantage in that animal experiments using rats, for example, can be carried out in advance, prior to testing pharmacological effects on human, and is useful in terms that clinical data on human can be easily predicted from the animal experiment data.

Since expression of the G protein-coupled receptor proteins of the invention in organs and changes thereof can be detected by the method such as ELISA, radioimmunoassay, the Western blotting and the like using the antibodies, these antibodies for the novel G-protein coupled receptor proteins are useful as diagnostic agents. In addition, the antibodies capable of modifying activities of the novel G protein-coupled receptor proteins are useful as therapeutic drugs for diseases in which the novel G protein-coupled receptor proteins are involved and also as tools for the separation and purification of the receptor proteins.

What is claimed is:

1. An isolated polynucleotide encoding a G protein-coupled receptor protein comprising amino acids 1 to 373 of SEQ ID NO:6.

2. The isolated polynucleotide encoding a G protein-coupled receptor protein of claim 1, which encodes a polypeptide consisting of amino acids 1 to 373 of SEQ ID NO:6.

3. An expression vector comprising the polynucleotide of claim 1 or claim 2.

4. A host cell transformed or transfected with the expression vector of claim 3.

5. A process for producing a recombinant host cell comprising transforming or transfecting a cell with the expression vector of claim 3 such that the host cell, under appropriate conditions, produces said G protein-coupled receptor protein.

6. A membrane of the recombinant host cell of claim 4 expressing said polypeptide.

7. A method for producing a G protein-coupled receptor protein comprising culturing the host cell of claim 4 under conditions sufficient for the production of said G protein-coupled receptor protein and recovering said protein from the culture.

8. A method for producing a G protein-coupled receptor protein which has the amino acid sequence comprising amino acids 1 to 373 of SEQ ID NO:6, comprising culturing the host cell of claim 4.

* * * * *

SEQUENCE LISTING

```
<160> NUMBER OF SEQ ID NOS: 26

<210> SEQ ID NO 1
<211> LENGTH: 1128
<212> TYPE: DNA
<213> ORGANISM: Homo sapiens
<220> FEATURE:
<221> NAME/KEY: CDS
<222> LOCATION: (1)..(1125)
<223> OTHER INFORMATION: SREB1

<400> SEQUENCE: 1

atg gcg aac gcg agc gag ccg ggt ggc agc ggc ggc ggc gag gcg gcc       48
Met Ala Asn Ala Ser Glu Pro Gly Gly Ser Gly Gly Gly Glu Ala Ala
  1               5                  10                  15

gcc ctg ggc ctc aag ctg gcc acg ctc agc ctg ctg ctg tgc gtg agc       96
Ala Leu Gly Leu Lys Leu Ala Thr Leu Ser Leu Leu Leu Cys Val Ser
             20                  25                  30

cta gcg ggc aac gtg ctg ttc gcg ctg ctg atc gtg cgg gag cgc agc      144
Leu Ala Gly Asn Val Leu Phe Ala Leu Leu Ile Val Arg Glu Arg Ser
         35                  40                  45

ctg cac cgc gcc ccg tac tac ctg ctg ctc gac ctg tgc ctg gcc gac      192
Leu His Arg Ala Pro Tyr Tyr Leu Leu Leu Asp Leu Cys Leu Ala Asp
     50                  55                  60

ggg ctg cgc gcg ctc gcc tgc ctc ccg gcc gtc atg ctg gcg gcg cgg      240
Gly Leu Arg Ala Leu Ala Cys Leu Pro Ala Val Met Leu Ala Ala Arg
 65                  70                  75                  80

cgt gcg gcg gcc gcg gcg ggg gcg ccg ccg ggc gcg ctg ggc tgc aag      288
Arg Ala Ala Ala Ala Ala Gly Ala Pro Pro Gly Ala Leu Gly Cys Lys
                 85                  90                  95

ctg ctc gcc ttc ctg gcc gcg ctc ttc tgc ttc cac gcc gcc ttc ctg      336
Leu Leu Ala Phe Leu Ala Ala Leu Phe Cys Phe His Ala Ala Phe Leu
            100                 105                 110

ctg ctg ggc gtg ggc gtc acc cgc tac ctg gcc atc gcg cac cac cgc      384
Leu Leu Gly Val Gly Val Thr Arg Tyr Leu Ala Ile Ala His His Arg
        115                 120                 125

ttc tat gca gag cgc ctg gcc ggc tgg ccg tgc gcc gcc atg ctg gtg      432
Phe Tyr Ala Glu Arg Leu Ala Gly Trp Pro Cys Ala Ala Met Leu Val
    130                 135                 140

tgc gcc gcc tgg gcg ctg gcg ctg gcc gcg gcc ttc ccg cca gtg ctg      480
Cys Ala Ala Trp Ala Leu Ala Leu Ala Ala Ala Phe Pro Pro Val Leu
145                 150                 155                 160

gac ggc ggt ggc gac gac gag gac gcg ccg tgc gcc ctg gag cag cgg      528
Asp Gly Gly Gly Asp Asp Glu Asp Ala Pro Cys Ala Leu Glu Gln Arg
                165                 170                 175

ccc gac ggc gcc ccc ggc gcg ctg ggc ttc ctg ctg ctg ctg gcc gtg      576
Pro Asp Gly Ala Pro Gly Ala Leu Gly Phe Leu Leu Leu Leu Ala Val
            180                 185                 190

gtg gtg ggc gcc acg cac ctc gtc tac ctc cgc ctg ctc ttc ttc atc      624
Val Val Gly Ala Thr His Leu Val Tyr Leu Arg Leu Leu Phe Phe Ile
        195                 200                 205

cac gac cgc cgc aag atg cgg ccc gcg cgc ctg gtg ccc gcc gtc agc      672
His Asp Arg Arg Lys Met Arg Pro Ala Arg Leu Val Pro Ala Val Ser
    210                 215                 220

cac gac tgg acc ttc cac ggc ccg ggc gcc acc ggc cag gcg gcc gcc      720
His Asp Trp Thr Phe His Gly Pro Gly Ala Thr Gly Gln Ala Ala Ala
225                 230                 235                 240

aac tgg acg gcg ggc ttc ggc cgc ggg ccc acg ccg ccc gcg ctt gtg      768
Asn Trp Thr Ala Gly Phe Gly Arg Gly Pro Thr Pro Pro Ala Leu Val
                245                 250                 255
```

-continued

```
ggc atc cgg ccc gca ggg ccg ggc cgc ggc gcg cgc cgc ctc ctc gtg      816
Gly Ile Arg Pro Ala Gly Pro Gly Arg Gly Ala Arg Arg Leu Leu Val
            260                 265                 270

ctg gaa gaa ttc aag acg gag aag agg ctg tgc aag atg ttc tac gcc      864
Leu Glu Glu Phe Lys Thr Glu Lys Arg Leu Cys Lys Met Phe Tyr Ala
        275                 280                 285

gtc acg ctg ctc ttc ctg ctc ctc tgg ggg ccc tac gtc gtg gcc agc      912
Val Thr Leu Leu Phe Leu Leu Leu Trp Gly Pro Tyr Val Val Ala Ser
    290                 295                 300

tac ctg cgg gtc ctg gtg cgg ccc ggc gcc gtc ccc cag gcc tac ctg      960
Tyr Leu Arg Val Leu Val Arg Pro Gly Ala Val Pro Gln Ala Tyr Leu
305                 310                 315                 320

acg gcc tcc gtg tgg ctg acc ttc gcg cag gcc ggc atc aac ccc gtc     1008
Thr Ala Ser Val Trp Leu Thr Phe Ala Gln Ala Gly Ile Asn Pro Val
                325                 330                 335

gtg tgc ttc ctc ttc aac agg gag ctg agg gac tgc ttc agg gcc cag     1056
Val Cys Phe Leu Phe Asn Arg Glu Leu Arg Asp Cys Phe Arg Ala Gln
            340                 345                 350

ttc ccc tgc tgc cag agc ccc cgg acc acc cag gcg acc cat ccc tgc     1104
Phe Pro Cys Cys Gln Ser Pro Arg Thr Thr Gln Ala Thr His Pro Cys
        355                 360                 365

gac ctg aaa ggc att ggt tta tga                                     1128
Asp Leu Lys Gly Ile Gly Leu
    370                 375


<210> SEQ ID NO 2
<211> LENGTH: 375
<212> TYPE: PRT
<213> ORGANISM: Homo sapiens

<400> SEQUENCE: 2

Met Ala Asn Ala Ser Glu Pro Gly Gly Ser Gly Gly Gly Glu Ala Ala
  1               5                  10                  15

Ala Leu Gly Leu Lys Leu Ala Thr Leu Ser Leu Leu Leu Cys Val Ser
            20                  25                  30

Leu Ala Gly Asn Val Leu Phe Ala Leu Leu Ile Val Arg Glu Arg Ser
        35                  40                  45

Leu His Arg Ala Pro Tyr Tyr Leu Leu Leu Asp Leu Cys Leu Ala Asp
     50                  55                  60

Gly Leu Arg Ala Leu Ala Cys Leu Pro Ala Val Met Leu Ala Ala Arg
 65                  70                  75                  80

Arg Ala Ala Ala Ala Ala Gly Ala Pro Pro Gly Ala Leu Gly Cys Lys
                 85                  90                  95

Leu Leu Ala Phe Leu Ala Ala Leu Phe Cys Phe His Ala Ala Phe Leu
            100                 105                 110

Leu Leu Gly Val Gly Val Thr Arg Tyr Leu Ala Ile Ala His His Arg
        115                 120                 125

Phe Tyr Ala Glu Arg Leu Ala Gly Trp Pro Cys Ala Ala Met Leu Val
    130                 135                 140

Cys Ala Ala Trp Ala Leu Ala Leu Ala Ala Ala Phe Pro Pro Val Leu
145                 150                 155                 160

Asp Gly Gly Gly Asp Asp Glu Asp Ala Pro Cys Ala Leu Glu Gln Arg
                165                 170                 175

Pro Asp Gly Ala Pro Gly Ala Leu Gly Phe Leu Leu Leu Leu Ala Val
            180                 185                 190

Val Val Gly Ala Thr His Leu Val Tyr Leu Arg Leu Leu Phe Phe Ile
        195                 200                 205
```

-continued

```
His Asp Arg Arg Lys Met Arg Pro Ala Arg Leu Val Pro Ala Val Ser
    210                 215                 220

His Asp Trp Thr Phe His Gly Pro Gly Ala Thr Gly Gln Ala Ala Ala
225                 230                 235                 240

Asn Trp Thr Ala Gly Phe Gly Arg Gly Pro Thr Pro Pro Ala Leu Val
                245                 250                 255

Gly Ile Arg Pro Ala Gly Pro Gly Arg Gly Ala Arg Arg Leu Leu Val
            260                 265                 270

Leu Glu Glu Phe Lys Thr Glu Lys Arg Leu Cys Lys Met Phe Tyr Ala
        275                 280                 285

Val Thr Leu Leu Phe Leu Leu Leu Trp Gly Pro Tyr Val Val Ala Ser
    290                 295                 300

Tyr Leu Arg Val Leu Val Arg Pro Gly Ala Val Pro Gln Ala Tyr Leu
305                 310                 315                 320

Thr Ala Ser Val Trp Leu Thr Phe Ala Gln Ala Gly Ile Asn Pro Val
                325                 330                 335

Val Cys Phe Leu Phe Asn Arg Glu Leu Arg Asp Cys Phe Arg Ala Gln
            340                 345                 350

Phe Pro Cys Cys Gln Ser Pro Arg Thr Thr Gln Ala Thr His Pro Cys
        355                 360                 365

Asp Leu Lys Gly Ile Gly Leu
    370                 375


<210> SEQ ID NO 3
<211> LENGTH: 1113
<212> TYPE: DNA
<213> ORGANISM: Homo sapiens
<220> FEATURE:
<221> NAME/KEY: CDS
<222> LOCATION: (1)..(1110)
<223> OTHER INFORMATION: SREB2

<400> SEQUENCE: 3

atg gcg aac tat agc cat gca gct gac aac att ttg caa aat ctc tcg       48
Met Ala Asn Tyr Ser His Ala Ala Asp Asn Ile Leu Gln Asn Leu Ser
  1               5                  10                  15

cct cta aca gcc ttt ctg aaa ctg act tcc ttg ggt ttc ata ata gga       96
Pro Leu Thr Ala Phe Leu Lys Leu Thr Ser Leu Gly Phe Ile Ile Gly
             20                  25                  30

gtc agc gtg gtg ggc aac ctc ctg atc tcc att ttg cta gtg aaa gat      144
Val Ser Val Val Gly Asn Leu Leu Ile Ser Ile Leu Leu Val Lys Asp
         35                  40                  45

aag acc ttg cat aga gca cct tac tac ttc ctg ttg gat ctt tgc tgt      192
Lys Thr Leu His Arg Ala Pro Tyr Tyr Phe Leu Leu Asp Leu Cys Cys
     50                  55                  60

tca gat atc ctc aga tct gca att tgt ttc cca ttt gtg ttc aac tct      240
Ser Asp Ile Leu Arg Ser Ala Ile Cys Phe Pro Phe Val Phe Asn Ser
 65                  70                  75                  80

gtc aaa aat ggc tct acc tgg act tat ggg act ctg act tgc aaa gtg      288
Val Lys Asn Gly Ser Thr Trp Thr Tyr Gly Thr Leu Thr Cys Lys Val
                 85                  90                  95

att gcc ttt ctg ggg gtt ttg tcc tgt ttc cac act gct ttc atg ctc      336
Ile Ala Phe Leu Gly Val Leu Ser Cys Phe His Thr Ala Phe Met Leu
            100                 105                 110

ttc tgc atc agt gtc acc aga tac tta gct atc gcc cat cac cgc ttc      384
Phe Cys Ile Ser Val Thr Arg Tyr Leu Ala Ile Ala His His Arg Phe
        115                 120                 125

tat aca aag agg ctg acc ttt tgg acg tgt ctg gct gtg atc tgt atg      432
```

```
Tyr Thr Lys Arg Leu Thr Phe Trp Thr Cys Leu Ala Val Ile Cys Met
    130                 135                 140

gtg tgg act ctg tct gtg gcc atg gca ttt ccc ccg gtt tta gac gtg      480
Val Trp Thr Leu Ser Val Ala Met Ala Phe Pro Pro Val Leu Asp Val
145                 150                 155                 160

ggc act tac tca ttc att agg gag gaa gat caa tgc acc ttc caa cac      528
Gly Thr Tyr Ser Phe Ile Arg Glu Glu Asp Gln Cys Thr Phe Gln His
                165                 170                 175

cgc tcc ttc agg gct aat gat tcc tta gga ttt atg ctg ctt ctt gct      576
Arg Ser Phe Arg Ala Asn Asp Ser Leu Gly Phe Met Leu Leu Leu Ala
            180                 185                 190

ctc atc ctc cta gcc aca cag ctt gtc tac ctc aag ctg ata ttt ttc      624
Leu Ile Leu Leu Ala Thr Gln Leu Val Tyr Leu Lys Leu Ile Phe Phe
        195                 200                 205

gtc cac gat cga aga aaa atg aag cca gtc cag ttt gta gca gca gtc      672
Val His Asp Arg Arg Lys Met Lys Pro Val Gln Phe Val Ala Ala Val
    210                 215                 220

agc cag aac tgg act ttt cat ggt cct gga gcc agt ggc cag gca gct      720
Ser Gln Asn Trp Thr Phe His Gly Pro Gly Ala Ser Gly Gln Ala Ala
225                 230                 235                 240

gcc aat tgg cta gca gga ttt gga agg ggt ccc aca cca ccc acc ttg      768
Ala Asn Trp Leu Ala Gly Phe Gly Arg Gly Pro Thr Pro Pro Thr Leu
                245                 250                 255

ctg ggc atc agg caa aat gca aac acc aca ggc aga aga agg cta ttg      816
Leu Gly Ile Arg Gln Asn Ala Asn Thr Thr Gly Arg Arg Arg Leu Leu
            260                 265                 270

gtc tta gac gag ttc aaa atg gag aaa aga atc agc aga atg ttc tat      864
Val Leu Asp Glu Phe Lys Met Glu Lys Arg Ile Ser Arg Met Phe Tyr
        275                 280                 285

ata atg act ttt ctg ttt cta acc ttg tgg ggc ccc tac ctg gtg gcc      912
Ile Met Thr Phe Leu Phe Leu Thr Leu Trp Gly Pro Tyr Leu Val Ala
    290                 295                 300

tgt tat tgg aga gtt ttt gca aga ggg cct gta gta cca ggg gga ttt      960
Cys Tyr Trp Arg Val Phe Ala Arg Gly Pro Val Val Pro Gly Gly Phe
305                 310                 315                 320

cta aca gct gct gtc tgg atg agt ttt gcc caa gca gga atc aat cct     1008
Leu Thr Ala Ala Val Trp Met Ser Phe Ala Gln Ala Gly Ile Asn Pro
                325                 330                 335

ttt gtc tgc att ttc tca aac agg gag ctg agg cgc tgt ttc agc aca     1056
Phe Val Cys Ile Phe Ser Asn Arg Glu Leu Arg Arg Cys Phe Ser Thr
            340                 345                 350

acc ctt ctt tac tgc aga aaa tcc agg tta cca agg gaa cct tac tgt     1104
Thr Leu Leu Tyr Cys Arg Lys Ser Arg Leu Pro Arg Glu Pro Tyr Cys
        355                 360                 365

gtt ata tga                                                         1113
Val Ile
    370


<210> SEQ ID NO 4
<211> LENGTH: 370
<212> TYPE: PRT
<213> ORGANISM: Homo sapiens

<400> SEQUENCE: 4

Met Ala Asn Tyr Ser His Ala Ala Asp Asn Ile Leu Gln Asn Leu Ser
  1               5                  10                  15

Pro Leu Thr Ala Phe Leu Lys Leu Thr Ser Leu Gly Phe Ile Ile Gly
            20                  25                  30

Val Ser Val Val Gly Asn Leu Leu Ile Ser Ile Leu Leu Val Lys Asp
        35                  40                  45
```

```
Lys Thr Leu His Arg Ala Pro Tyr Tyr Phe Leu Leu Asp Leu Cys Cys
     50                  55                  60

Ser Asp Ile Leu Arg Ser Ala Ile Cys Phe Pro Phe Val Phe Asn Ser
 65                  70                  75                  80

Val Lys Asn Gly Ser Thr Trp Thr Tyr Gly Thr Leu Thr Cys Lys Val
                 85                  90                  95

Ile Ala Phe Leu Gly Val Leu Ser Cys Phe His Thr Ala Phe Met Leu
            100                 105                 110

Phe Cys Ile Ser Val Thr Arg Tyr Leu Ala Ile Ala His His Arg Phe
        115                 120                 125

Tyr Thr Lys Arg Leu Thr Phe Trp Thr Cys Leu Ala Val Ile Cys Met
    130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
                165                 170                 175

Arg Ser Phe Arg Ala Asn Asp Ser Leu Gly Phe Met Leu Leu Leu Ala
            180                 185                 190

Leu Ile Leu Leu Ala Thr Gln Leu Val Tyr Leu Lys Leu Ile Phe Phe
        195                 200                 205

Val His Asp Arg Arg Lys Met Lys Pro Val Gln Phe Val Ala Ala Val
    210                 215                 220

Ser Gln Asn Trp Thr Phe His Gly Pro Gly Ala Ser Gly Gln Ala Ala
225                 230                 235                 240

Ala Asn Trp Leu Ala Gly Phe Gly Arg Gly Pro Thr Pro Pro Thr Leu
                245                 250                 255

Leu Gly Ile Arg Gln Asn Ala Asn Thr Thr Gly Arg Arg Arg Leu Leu
            260                 265                 270

Val Leu Asp Glu Phe Lys Met Glu Lys Arg Ile Ser Arg Met Phe Tyr
        275                 280                 285

Ile Met Thr Phe Leu Phe Leu Thr Leu Trp Gly Pro Tyr Leu Val Ala
    290                 295                 300

Cys Tyr Trp Arg Val Phe Ala Arg Gly Pro Val Val Pro Gly Gly Phe
305                 310                 315                 320

Leu Thr Ala Ala Val Trp Met Ser Phe Ala Gln Ala Gly Ile Asn Pro
                325                 330                 335

Phe Val Cys Ile Phe Ser Asn Arg Glu Leu Arg Arg Cys Phe Ser Thr
            340                 345                 350

Thr Leu Leu Tyr Cys Arg Lys Ser Arg Leu Pro Arg Glu Pro Tyr Cys
        355                 360                 365

Val Ile
    370


<210> SEQ ID NO 5
<211> LENGTH: 1122
<212> TYPE: DNA
<213> ORGANISM: Homo sapiens
<220> FEATURE:
<221> NAME/KEY: CDS
<222> LOCATION: (1)..(1119)
<223> OTHER INFORMATION: SREB3

<400> SEQUENCE: 5

atg gcc aac act acc gga gag cct gag gag gtg agc ggc gct ctg tcc       48
Met Ala Asn Thr Thr Gly Glu Pro Glu Glu Val Ser Gly Ala Leu Ser
  1               5                  10                  15
```

-continued

```
cca ccg tcc gca tca gct tat gtg aag ctg gta ctg ctg gga ctg att       96
Pro Pro Ser Ala Ser Ala Tyr Val Lys Leu Val Leu Leu Gly Leu Ile
             20                  25                  30

atg tgc gtg agc ctg gcg ggt aac gcc atc ttg tcc ctg ctg gtg ctc      144
Met Cys Val Ser Leu Ala Gly Asn Ala Ile Leu Ser Leu Leu Val Leu
         35                  40                  45

aag gag cgt gcc ctg cac aag gct cct tac tac ttc ctg ctg gac ctg      192
Lys Glu Arg Ala Leu His Lys Ala Pro Tyr Tyr Phe Leu Leu Asp Leu
     50                  55                  60

tgc ctg gcc gat ggc ata cgc tct gcc gtc tgc ttc ccc ttt gtg ctg      240
Cys Leu Ala Asp Gly Ile Arg Ser Ala Val Cys Phe Pro Phe Val Leu
 65                  70                  75                  80

gct tct gtg cgc cac ggc tct tca tgg acc ttc agt gca ctc agc tgc      288
Ala Ser Val Arg His Gly Ser Ser Trp Thr Phe Ser Ala Leu Ser Cys
                 85                  90                  95

aag att gtg gcc ttt atg gcc gtg ctc ttt tgc ttc cat gcg gcc ttc      336
Lys Ile Val Ala Phe Met Ala Val Leu Phe Cys Phe His Ala Ala Phe
            100                 105                 110

atg ctg ttc tgc atc agc gtc acc cgc tac atg gcc atc gcc cac cac      384
Met Leu Phe Cys Ile Ser Val Thr Arg Tyr Met Ala Ile Ala His His
        115                 120                 125

cgc ttc tac gcc aag cgc atg aca ctc tgg aca tgc gcg gct gtc atc      432
Arg Phe Tyr Ala Lys Arg Met Thr Leu Trp Thr Cys Ala Ala Val Ile
    130                 135                 140

tgc atg gcc tgg acc ctg tct gtg gcc atg gcc ttc cca cct gtc ttt      480
Cys Met Ala Trp Thr Leu Ser Val Ala Met Ala Phe Pro Pro Val Phe
145                 150                 155                 160

gac gtg ggc acc tac aag ttt att cgg gag gag gac cag tgc atc ttt      528
Asp Val Gly Thr Tyr Lys Phe Ile Arg Glu Glu Asp Gln Cys Ile Phe
                165                 170                 175

gag cat cgc tac ttc aag gcc aat gac acg ctg ggc ttc atg ctt atg      576
Glu His Arg Tyr Phe Lys Ala Asn Asp Thr Leu Gly Phe Met Leu Met
            180                 185                 190

ttg gct gtg ctc atg gca gct acc cat gct gtc tac ggc aag ctg ctc      624
Leu Ala Val Leu Met Ala Ala Thr His Ala Val Tyr Gly Lys Leu Leu
        195                 200                 205

ctc ttc gag tat cgt cac cgc aag atg aag cca gtg cag atg gtg cca      672
Leu Phe Glu Tyr Arg His Arg Lys Met Lys Pro Val Gln Met Val Pro
    210                 215                 220

gcc atc agc cag aac tgg aca ttc cat ggt ccc ggg gcc acc ggc cag      720
Ala Ile Ser Gln Asn Trp Thr Phe His Gly Pro Gly Ala Thr Gly Gln
225                 230                 235                 240

gct gct gcc aac tgg atc gcc ggc ttt ggc cgt ggg ccc atg cca cca      768
Ala Ala Ala Asn Trp Ile Ala Gly Phe Gly Arg Gly Pro Met Pro Pro
                245                 250                 255

acc ctg ctg ggt atc cgg cag aat ggg cat gca gcc agc cgg cgg cta      816
Thr Leu Leu Gly Ile Arg Gln Asn Gly His Ala Ala Ser Arg Arg Leu
            260                 265                 270

ctg ggc atg gac gag gtc aag ggt gaa aag cag ctg ggc cgc atg ttc      864
Leu Gly Met Asp Glu Val Lys Gly Glu Lys Gln Leu Gly Arg Met Phe
        275                 280                 285

tac gcg atc aca ctg ctc ttt ctg ctc ctc tgg tca ccc tac atc gtg      912
Tyr Ala Ile Thr Leu Leu Phe Leu Leu Leu Trp Ser Pro Tyr Ile Val
    290                 295                 300

gcc tgc tac tgg cga gtg ttt gtg aaa gcc tgt gct gtg ccc cac cgc      960
Ala Cys Tyr Trp Arg Val Phe Val Lys Ala Cys Ala Val Pro His Arg
305                 310                 315                 320

tac ctg gcc act gct gtt tgg atg agc ttc gcc cag gct gcc gtc aac     1008
Tyr Leu Ala Thr Ala Val Trp Met Ser Phe Ala Gln Ala Ala Val Asn
```

-continued

```
                325                 330                 335

cca att gtc tgc ttc ctg ctc aac aag gac ctc aag aag tgc ctg agg      1056
Pro Ile Val Cys Phe Leu Leu Asn Lys Asp Leu Lys Lys Cys Leu Arg
            340                 345                 350

act cac gcc ccc tgc tgg ggc aca gga ggt gcc ccg gct ccc aga gaa      1104
Thr His Ala Pro Cys Trp Gly Thr Gly Gly Ala Pro Ala Pro Arg Glu
        355                 360                 365

ccc tac tgt gtc atg tga                                              1122
Pro Tyr Cys Val Met
    370


<210> SEQ ID NO 6
<211> LENGTH: 373
<212> TYPE: PRT
<213> ORGANISM: Homo sapiens

<400> SEQUENCE: 6

Met Ala Asn Thr Thr Gly Glu Pro Glu Glu Val Ser Gly Ala Leu Ser
  1               5                  10                  15

Pro Pro Ser Ala Ser Ala Tyr Val Lys Leu Val Leu Leu Gly Leu Ile
            20                  25                  30

Met Cys Val Ser Leu Ala Gly Asn Ala Ile Leu Ser Leu Leu Val Leu
        35                  40                  45

Lys Glu Arg Ala Leu His Lys Ala Pro Tyr Tyr Phe Leu Leu Asp Leu
    50                  55                  60

Cys Leu Ala Asp Gly Ile Arg Ser Ala Val Cys Phe Pro Phe Val Leu
 65                  70                  75                  80

Ala Ser Val Arg His Gly Ser Ser Trp Thr Phe Ser Ala Leu Ser Cys
                 85                  90                  95

Lys Ile Val Ala Phe Met Ala Val Leu Phe Cys Phe His Ala Ala Phe
            100                 105                 110

Met Leu Phe Cys Ile Ser Val Thr Arg Tyr Met Ala Ile Ala His His
        115                 120                 125

Arg Phe Tyr Ala Lys Arg Met Thr Leu Trp Thr Cys Ala Ala Val Ile
    130                 135                 140

Cys Met Ala Trp Thr Leu Ser Val Ala Met Ala Phe Pro Pro Val Phe
145                 150                 155                 160

Asp Val Gly Thr Tyr Lys Phe Ile Arg Glu Glu Asp Gln Cys Ile Phe
                165                 170                 175

Glu His Arg Tyr Phe Lys Ala Asn Asp Thr Leu Gly Phe Met Leu Met
            180                 185                 190

Leu Ala Val Leu Met Ala Ala Thr His Ala Val Tyr Gly Lys Leu Leu
        195                 200                 205

Leu Phe Glu Tyr Arg His Arg Lys Met Lys Pro Val Gln Met Val Pro
    210                 215                 220

Ala Ile Ser Gln Asn Trp Thr Phe His Gly Pro Gly Ala Thr Gly Gln
225                 230                 235                 240

Ala Ala Ala Asn Trp Ile Ala Gly Phe Gly Arg Gly Pro Met Pro Pro
                245                 250                 255

Thr Leu Leu Gly Ile Arg Gln Asn Gly His Ala Ala Ser Arg Arg Leu
            260                 265                 270

Leu Gly Met Asp Glu Val Lys Gly Glu Lys Gln Leu Gly Arg Met Phe
        275                 280                 285

Tyr Ala Ile Thr Leu Leu Phe Leu Leu Leu Trp Ser Pro Tyr Ile Val
    290                 295                 300
```

-continued

```
Ala Cys Tyr Trp Arg Val Phe Val Lys Ala Cys Ala Val Pro His Arg
305                 310                 315                 320

Tyr Leu Ala Thr Ala Val Trp Met Ser Phe Ala Gln Ala Ala Val Asn
                325                 330                 335

Pro Ile Val Cys Phe Leu Leu Asn Lys Asp Leu Lys Lys Cys Leu Arg
            340                 345                 350

Thr His Ala Pro Cys Trp Gly Thr Gly Gly Ala Pro Ala Pro Arg Glu
        355                 360                 365

Pro Tyr Cys Val Met
    370


<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:Forward
      primer

<400> SEQUENCE: 7

aaaatctaga cgcgatggcg aacgcgagcg a                                     31


<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:reverse
      primer

<400> SEQUENCE: 8

aaaatctaga gtctatgtgg cggggcctcc c                                     31


<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence:Forward
      primer

<400> SEQUENCE: 9

aaaatctaga tctatggcga actatagcca tgca                                  34


<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:reverse
      primer

<400> SEQUENCE: 10

aaaatctaga aaggctaaag atttacagat gctcc                                 35


<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:Forward
      primer

<400> SEQUENCE: 11

aaaatctaga gtatggccaa cactaccgga gag                                   33
```

-continued

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:reverse primer

<400> SEQUENCE: 12
aaaatctaga cctgtctgcc taccagcctg c 31

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:FLAG epitope

<400> SEQUENCE: 13
atggactaca aggacgacga tgacaagggg atcctg 36

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence:FLAG epitope

<400> SEQUENCE: 14

Met Asp Tyr Lys Asp Asp Asp Asp Lys Gly Ile Leu
1 5 10

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:Forward primer

<400> SEQUENCE: 15
aaaatctaga cggcgatggc gaacgctagt ga 32

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:reverse primer

<400> SEQUENCE: 16
aaaatctaga cactttgaga gtcttgtgaa ggc 33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:Forward primer

<400> SEQUENCE: 17
aaaatctaga tctatggcga actatagcca tgc 33

```
<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence:Forward
      primer

<400> SEQUENCE: 18

aaaatctaga aaggctaaag atttacagat gctcc                                35


<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:reverse
      primer

<400> SEQUENCE: 19

aaaatctaga caaatactga actggccgat cccc                                 34


<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:reverse
      primer

<400> SEQUENCE: 20

aaaatctaga tgttggcccc agtatggtga tcat                                 34


<210> SEQ ID NO 21
<211> LENGTH: 1134
<212> TYPE: DNA
<213> ORGANISM: Rattus sp.
<220> FEATURE:
<221> NAME/KEY: CDS
<222> LOCATION: (1)..(1131)
<223> OTHER INFORMATION: Rat SREB1

<400> SEQUENCE: 21

atg gcg aac gct agt gag ccg ggc ggc ggc ggc ggc ggg gcc gag gct       48
Met Ala Asn Ala Ser Glu Pro Gly Gly Gly Gly Gly Gly Ala Glu Ala
  1               5                  10                  15

gcc gcg ctg ggc ctc agg ctg gcc aca ctc agc ctg ctg ctg tgc gtg       96
Ala Ala Leu Gly Leu Arg Leu Ala Thr Leu Ser Leu Leu Leu Cys Val
             20                  25                  30

agc ctg gcg ggc aac gtg ctg ttc gct ctg ctc atc gtg agg gag cgc      144
Ser Leu Ala Gly Asn Val Leu Phe Ala Leu Leu Ile Val Arg Glu Arg
         35                  40                  45

agc ctg cac cgc gcg cct tac tac ctg ctg ctc gac ctg tgc ctg gcc      192
Ser Leu His Arg Ala Pro Tyr Tyr Leu Leu Leu Asp Leu Cys Leu Ala
     50                  55                  60

gac ggg ctg cgc gcg ctc gcc tgt ctc ccg gcc gtc atg ctg gct gcg      240
Asp Gly Leu Arg Ala Leu Ala Cys Leu Pro Ala Val Met Leu Ala Ala
 65                  70                  75                  80

cgg cgc gcg gca gcc gcg gcg ggg acg cct ccg ggt gcg ctg ggc tgc      288
Arg Arg Ala Ala Ala Ala Ala Gly Thr Pro Pro Gly Ala Leu Gly Cys
                 85                  90                  95

aag ctg ctg gcc ttc ctg gcc gcg ctc ttc tgc ttc cac gcg gcc ttc      336
Lys Leu Leu Ala Phe Leu Ala Ala Leu Phe Cys Phe His Ala Ala Phe
            100                 105                 110

ctg ctg ctg ggc gtg ggc gtc acc cgc tac ctg gcc atc gct cac cac      384
```

-continued

```
Leu Leu Leu Gly Val Gly Val Thr Arg Tyr Leu Ala Ile Ala His His
        115                 120                 125

cgc ttc tat gcc gag cgc ctg gcc ggc tgg ccg tgc gcc gcg atg ctg      432
Arg Phe Tyr Ala Glu Arg Leu Ala Gly Trp Pro Cys Ala Ala Met Leu
    130                 135                 140

gtg tgc gcc gcc tgg gcg ctg gct ttg gcc gcg gcc ttc ccg ccg gtg      480
Val Cys Ala Ala Trp Ala Leu Ala Leu Ala Ala Ala Phe Pro Pro Val
145                 150                 155                 160

ctg gac ggc ggt ggc gcg gac gac gag gat gcg ccg tgc gcc ctg gag      528
Leu Asp Gly Gly Gly Ala Asp Asp Glu Asp Ala Pro Cys Ala Leu Glu
                165                 170                 175

cag cgg ccc gac ggc gcc ccg ggt gcg cta ggc ttc ctg ctg ctc ctg      576
Gln Arg Pro Asp Gly Ala Pro Gly Ala Leu Gly Phe Leu Leu Leu Leu
            180                 185                 190

gcc gcg gtg gtg ggc gcc acg cac ctc gtc tac ctt cgc ctg ctc ttc      624
Ala Ala Val Val Gly Ala Thr His Leu Val Tyr Leu Arg Leu Leu Phe
        195                 200                 205

ttc atc cac gac cgc cgc aag atg cgg ccc gca cgc ctg gtg ccc gcc      672
Phe Ile His Asp Arg Arg Lys Met Arg Pro Ala Arg Leu Val Pro Ala
    210                 215                 220

gtc agc cac gac tgg acc ttc cac ggc ccg ggc gcc acc ggt caa gcg      720
Val Ser His Asp Trp Thr Phe His Gly Pro Gly Ala Thr Gly Gln Ala
225                 230                 235                 240

gcc gcc aac tgg acg gcg ggc ttc ggc cgc ggg ccc acg cca cct gcg      768
Ala Ala Asn Trp Thr Ala Gly Phe Gly Arg Gly Pro Thr Pro Pro Ala
                245                 250                 255

ctc gtg ggc atc agg cct gca ggc ccg ggc cgc gga gcc cgg cgc ctc      816
Leu Val Gly Ile Arg Pro Ala Gly Pro Gly Arg Gly Ala Arg Arg Leu
            260                 265                 270

ctg gtg ctg gag gaa ttc aag acg gag aag agg ctg tgc aag atg ttc      864
Leu Val Leu Glu Glu Phe Lys Thr Glu Lys Arg Leu Cys Lys Met Phe
        275                 280                 285

tac gcc atc acg ctg ctc ttc ctg ctc ctc tgg ggg ccc tat gtg gtt      912
Tyr Ala Ile Thr Leu Leu Phe Leu Leu Leu Trp Gly Pro Tyr Val Val
    290                 295                 300

gcc agt tac ctg cgc gtc ctg gtg cgg ccc gga gct gtc ccg cag gcc      960
Ala Ser Tyr Leu Arg Val Leu Val Arg Pro Gly Ala Val Pro Gln Ala
305                 310                 315                 320

tac ctg aca gcc tcg gtg tgg ctg aca ttc gca cag gcc ggc atc aac     1008
Tyr Leu Thr Ala Ser Val Trp Leu Thr Phe Ala Gln Ala Gly Ile Asn
                325                 330                 335

ccc gtg gtg tgt ttc ctc ttc aac cgg gag ctg agg gac tgt ttc aga     1056
Pro Val Val Cys Phe Leu Phe Asn Arg Glu Leu Arg Asp Cys Phe Arg
            340                 345                 350

gcc cag ttc ccc tgt tgc cag agc ccc cag gcc acg cag gcc acc ctc     1104
Ala Gln Phe Pro Cys Cys Gln Ser Pro Gln Ala Thr Gln Ala Thr Leu
        355                 360                 365

ccc tgc gac ctg aaa ggc att ggt ttg tga                              1134
Pro Cys Asp Leu Lys Gly Ile Gly Leu
    370                 375

<210> SEQ ID NO 22
<211> LENGTH: 377
<212> TYPE: PRT
<213> ORGANISM: Rattus sp.

<400> SEQUENCE: 22

Met Ala Asn Ala Ser Glu Pro Gly Gly Gly Gly Gly Gly Ala Glu Ala
  1               5                  10                  15

Ala Ala Leu Gly Leu Arg Leu Ala Thr Leu Ser Leu Leu Leu Cys Val
```

-continued

```
            20                  25                  30

Ser Leu Ala Gly Asn Val Leu Phe Ala Leu Leu Ile Val Arg Glu Arg
        35                  40                  45

Ser Leu His Arg Ala Pro Tyr Tyr Leu Leu Leu Asp Leu Cys Leu Ala
    50                  55                  60

Asp Gly Leu Arg Ala Leu Ala Cys Leu Pro Ala Val Met Leu Ala Ala
65                  70                  75                  80

Arg Arg Ala Ala Ala Ala Ala Gly Thr Pro Pro Gly Ala Leu Gly Cys
                85                  90                  95

Lys Leu Leu Ala Phe Leu Ala Ala Leu Phe Cys Phe His Ala Ala Phe
            100                 105                 110

Leu Leu Leu Gly Val Gly Val Thr Arg Tyr Leu Ala Ile Ala His His
        115                 120                 125

Arg Phe Tyr Ala Glu Arg Leu Ala Gly Trp Pro Cys Ala Ala Met Leu
    130                 135                 140

Val Cys Ala Ala Trp Ala Leu Ala Leu Ala Ala Ala Phe Pro Pro Val
145                 150                 155                 160

Leu Asp Gly Gly Gly Ala Asp Asp Glu Asp Ala Pro Cys Ala Leu Glu
                165                 170                 175

Gln Arg Pro Asp Gly Ala Pro Gly Ala Leu Gly Phe Leu Leu Leu Leu
            180                 185                 190

Ala Ala Val Val Gly Ala Thr His Leu Val Tyr Leu Arg Leu Leu Phe
        195                 200                 205

Phe Ile His Asp Arg Arg Lys Met Arg Pro Ala Arg Leu Val Pro Ala
    210                 215                 220

Val Ser His Asp Trp Thr Phe His Gly Pro Gly Ala Thr Gly Gln Ala
225                 230                 235                 240

Ala Ala Asn Trp Thr Ala Gly Phe Gly Arg Gly Pro Thr Pro Pro Ala
                245                 250                 255

Leu Val Gly Ile Arg Pro Ala Gly Pro Gly Arg Gly Ala Arg Arg Leu
            260                 265                 270

Leu Val Leu Glu Glu Phe Lys Thr Glu Lys Arg Leu Cys Lys Met Phe
        275                 280                 285

Tyr Ala Ile Thr Leu Leu Phe Leu Leu Leu Trp Gly Pro Tyr Val Val
    290                 295                 300

Ala Ser Tyr Leu Arg Val Leu Val Arg Pro Gly Ala Val Pro Gln Ala
305                 310                 315                 320

Tyr Leu Thr Ala Ser Val Trp Leu Thr Phe Ala Gln Ala Gly Ile Asn
                325                 330                 335

Pro Val Val Cys Phe Leu Phe Asn Arg Glu Leu Arg Asp Cys Phe Arg
            340                 345                 350

Ala Gln Phe Pro Cys Cys Gln Ser Pro Gln Ala Thr Gln Ala Thr Leu
        355                 360                 365

Pro Cys Asp Leu Lys Gly Ile Gly Leu
    370                 375
```

<210> SEQ ID NO 23
<211> LENGTH: 1113
<212> TYPE: DNA
<213> ORGANISM: Rattus sp.
<220> FEATURE:
<221> NAME/KEY: CDS
<222> LOCATION: (1)..(1110)
<223> OTHER INFORMATION: Rat SREB2

<400> SEQUENCE: 23

-continued

```
atg gcg aac tat agc cat gca gct gac aac att ttg caa aat ctc tcg       48
Met Ala Asn Tyr Ser His Ala Ala Asp Asn Ile Leu Gln Asn Leu Ser
  1               5                  10                  15

cct cta aca gcc ttt ctg aaa ctg act tcc ttg ggt ttc ata ata gga       96
Pro Leu Thr Ala Phe Leu Lys Leu Thr Ser Leu Gly Phe Ile Ile Gly
             20                  25                  30

gtc agt gtg gtg ggc aac ctt ctg atc tcc att ttg cta gtg aaa gat      144
Val Ser Val Val Gly Asn Leu Leu Ile Ser Ile Leu Leu Val Lys Asp
         35                  40                  45

aag acc ttg cat aga gct cct tac tac ttc ctg ctg gat ctg tgc tgc      192
Lys Thr Leu His Arg Ala Pro Tyr Tyr Phe Leu Leu Asp Leu Cys Cys
     50                  55                  60

tca gac atc ctc aga tct gca att tgt ttt cca ttt gta ttc aac tct      240
Ser Asp Ile Leu Arg Ser Ala Ile Cys Phe Pro Phe Val Phe Asn Ser
 65                  70                  75                  80

gtc aaa aat ggc tct acc tgg act tac ggg act ctg act tgc aaa gtg      288
Val Lys Asn Gly Ser Thr Trp Thr Tyr Gly Thr Leu Thr Cys Lys Val
                 85                  90                  95

att gcc ttt ctg ggg gtt ttg tcc tgt ttc cac act gcc ttc atg ctc      336
Ile Ala Phe Leu Gly Val Leu Ser Cys Phe His Thr Ala Phe Met Leu
            100                 105                 110

ttc tgc atc agc gtc acc aga tac tta gcc atc gcc cat cac cgc ttc      384
Phe Cys Ile Ser Val Thr Arg Tyr Leu Ala Ile Ala His His Arg Phe
        115                 120                 125

tat aca aag agg ctg acc ttt tgg acg tgt ttg gct gtg atc tgc atg      432
Tyr Thr Lys Arg Leu Thr Phe Trp Thr Cys Leu Ala Val Ile Cys Met
    130                 135                 140

gtg tgg act ctg tct gtg gcc atg gca ttt ccc cca gtt tta gat gta      480
Val Trp Thr Leu Ser Val Ala Met Ala Phe Pro Pro Val Leu Asp Val
145                 150                 155                 160

ggc acc tac tca ttc att agg gag gag gat cag tgt acc ttc caa cac      528
Gly Thr Tyr Ser Phe Ile Arg Glu Glu Asp Gln Cys Thr Phe Gln His
                165                 170                 175

cgc tcc ttc agg gct aac gat tcc cta gga ttt atg ctg ctc ctt gct      576
Arg Ser Phe Arg Ala Asn Asp Ser Leu Gly Phe Met Leu Leu Leu Ala
            180                 185                 190

ctc atc ctc cta gcc aca cag ctt gtc tac ctc aag ctg ata ttt ttt      624
Leu Ile Leu Leu Ala Thr Gln Leu Val Tyr Leu Lys Leu Ile Phe Phe
        195                 200                 205

gtc cac gat cga agg aaa atg aag cca gtc cag ttt gta gca gca gtg      672
Val His Asp Arg Arg Lys Met Lys Pro Val Gln Phe Val Ala Ala Val
    210                 215                 220

agt cag aac tgg acc ttt cat ggc cct gga gct agt ggc cag gca gct      720
Ser Gln Asn Trp Thr Phe His Gly Pro Gly Ala Ser Gly Gln Ala Ala
225                 230                 235                 240

gcc aat tgg cta gca gga ttt gga agg ggt ccc aca cca ccc acc ttg      768
Ala Asn Trp Leu Ala Gly Phe Gly Arg Gly Pro Thr Pro Pro Thr Leu
                245                 250                 255

ctg ggc atc agg caa aat gcg aat acc aca ggc aga aga cgg ctc ttg      816
Leu Gly Ile Arg Gln Asn Ala Asn Thr Thr Gly Arg Arg Arg Leu Leu
            260                 265                 270

gtt ttg gat gag ttc aaa atg gag aaa aga atc agc aga atg ttc tat      864
Val Leu Asp Glu Phe Lys Met Glu Lys Arg Ile Ser Arg Met Phe Tyr
        275                 280                 285

ata atg act ttc ctc ttc cta acc ttg tgg ggt ccc tac ctg gtg gcc      912
Ile Met Thr Phe Leu Phe Leu Thr Leu Trp Gly Pro Tyr Leu Val Ala
    290                 295                 300

tgc tat tgg aga gtt ttt gca aga ggg cct gta gta cca ggg gga ttt      960
Cys Tyr Trp Arg Val Phe Ala Arg Gly Pro Val Val Pro Gly Gly Phe
```

-continued

```
305                 310                 315                 320

cta aca gcc gct gtc tgg atg agt ttc gcc caa gca gga atc aat ccc     1008
Leu Thr Ala Ala Val Trp Met Ser Phe Ala Gln Ala Gly Ile Asn Pro
                325                 330                 335

ttt gtc tgc att ttc tcc aac agg gag ctg agg cgc tgt ttc agc aca     1056
Phe Val Cys Ile Phe Ser Asn Arg Glu Leu Arg Arg Cys Phe Ser Thr
            340                 345                 350

acc ctt ctt tac tgc aga aaa tcc agg tta cca agg gaa cct tac tgt     1104
Thr Leu Leu Tyr Cys Arg Lys Ser Arg Leu Pro Arg Glu Pro Tyr Cys
        355                 360                 365

gtt ata tga                                                         1113
Val Ile
    370


<210> SEQ ID NO 24
<211> LENGTH: 370
<212> TYPE: PRT
<213> ORGANISM: Rattus sp.

<400> SEQUENCE: 24

Met Ala Asn Tyr Ser His Ala Ala Asp Asn Ile Leu Gln Asn Leu Ser
  1               5                  10                  15

Pro Leu Thr Ala Phe Leu Lys Leu Thr Ser Leu Gly Phe Ile Ile Gly
            20                  25                  30

Val Ser Val Val Gly Asn Leu Leu Ile Ser Ile Leu Leu Val Lys Asp
        35                  40                  45

Lys Thr Leu His Arg Ala Pro Tyr Tyr Phe Leu Leu Asp Leu Cys Cys
    50                  55                  60

Ser Asp Ile Leu Arg Ser Ala Ile Cys Phe Pro Phe Val Phe Asn Ser
 65                  70                  75                  80

Val Lys Asn Gly Ser Thr Trp Thr Tyr Gly Thr Leu Thr Cys Lys Val
                85                  90                  95

Ile Ala Phe Leu Gly Val Leu Ser Cys Phe His Thr Ala Phe Met Leu
            100                 105                 110

Phe Cys Ile Ser Val Thr Arg Tyr Leu Ala Ile Ala His His Arg Phe
        115                 120                 125

Tyr Thr Lys Arg Leu Thr Phe Trp Thr Cys Leu Ala Val Ile Cys Met
    130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
                165                 170                 175

Arg Ser Phe Arg Ala Asn Asp Ser Leu Gly Phe Met Leu Leu Leu Ala
            180                 185                 190

Leu Ile Leu Leu Ala Thr Gln Leu Val Tyr Leu Lys Leu Ile Phe Phe
        195                 200                 205

Val His Asp Arg Arg Lys Met Lys Pro Val Gln Phe Val Ala Ala Val
    210                 215                 220

Ser Gln Asn Trp Thr Phe His Gly Pro Gly Ala Ser Gly Gln Ala Ala
225                 230                 235                 240

Ala Asn Trp Leu Ala Gly Phe Gly Arg Gly Pro Thr Pro Pro Thr Leu
                245                 250                 255

Leu Gly Ile Arg Gln Asn Ala Asn Thr Thr Gly Arg Arg Arg Leu Leu
            260                 265                 270

Val Leu Asp Glu Phe Lys Met Glu Lys Arg Ile Ser Arg Met Phe Tyr
        275                 280                 285
```

```
Ile Met Thr Phe Leu Phe Leu Thr Leu Trp Gly Pro Tyr Leu Val Ala
    290                 295                 300

Cys Tyr Trp Arg Val Phe Ala Arg Gly Pro Val Val Pro Gly Gly Phe
305                 310                 315                 320

Leu Thr Ala Ala Val Trp Met Ser Phe Ala Gln Ala Gly Ile Asn Pro
                325                 330                 335

Phe Val Cys Ile Phe Ser Asn Arg Glu Leu Arg Arg Cys Phe Ser Thr
            340                 345                 350

Thr Leu Leu Tyr Cys Arg Lys Ser Arg Leu Pro Arg Glu Pro Tyr Cys
        355                 360                 365

Val Ile
    370


<210> SEQ ID NO 25
<211> LENGTH: 1122
<212> TYPE: DNA
<213> ORGANISM: Rat coronavirus
<220> FEATURE:
<221> NAME/KEY: CDS
<222> LOCATION: (1)..(1119)
<223> OTHER INFORMATION: Rat SREB3

<400> SEQUENCE: 25

atg gcc aac acc acc gga gag ccc gaa gag gtg agc ggc gca ctg tcc       48
Met Ala Asn Thr Thr Gly Glu Pro Glu Glu Val Ser Gly Ala Leu Ser
  1               5                  10                  15

ctg cca tca gca tcg gct tat gtg aag ctg gtg ctg ctg gga ctg atc       96
Leu Pro Ser Ala Ser Ala Tyr Val Lys Leu Val Leu Leu Gly Leu Ile
             20                  25                  30

atg tgt gta agc ctg gca ggc aat gcc atc ttg tcc ctg ctg gtg ctc      144
Met Cys Val Ser Leu Ala Gly Asn Ala Ile Leu Ser Leu Leu Val Leu
         35                  40                  45

aag gag cgt gcc ctg cac aag gct cct tac tac ttt ctg ctg gac ctg      192
Lys Glu Arg Ala Leu His Lys Ala Pro Tyr Tyr Phe Leu Leu Asp Leu
     50                  55                  60

tgc cta gcc gat ggc ata cgc tct gcc atc tgc ttc ccc ttt gta ctg      240
Cys Leu Ala Asp Gly Ile Arg Ser Ala Ile Cys Phe Pro Phe Val Leu
 65                  70                  75                  80

gct tct gtg cgc cat ggc tcc tcg tgg acc ttc agt gca ctc agc tgt      288
Ala Ser Val Arg His Gly Ser Ser Trp Thr Phe Ser Ala Leu Ser Cys
                 85                  90                  95

aag att gtg gcc ttt atg gct gtg ctc ttt tgc ttc cat gcg gcc ttc      336
Lys Ile Val Ala Phe Met Ala Val Leu Phe Cys Phe His Ala Ala Phe
            100                 105                 110

atg ctg ttc tgc atc agc gtc acc cgc tac atg gcc atc gcc cac cac      384
Met Leu Phe Cys Ile Ser Val Thr Arg Tyr Met Ala Ile Ala His His
        115                 120                 125

cgc ttc tat gcc aag cgc atg aca ctc tgg aca tgc gca gct gtc atc      432
Arg Phe Tyr Ala Lys Arg Met Thr Leu Trp Thr Cys Ala Ala Val Ile
    130                 135                 140

tgc atg gcc tgg acc ttg tct gtg gcc atg gct ttc cca cct gtc ttt      480
Cys Met Ala Trp Thr Leu Ser Val Ala Met Ala Phe Pro Pro Val Phe
145                 150                 155                 160

gat gtg ggc acc tac aag ttt atc cga gag gag gac cag tgc atc ttt      528
Asp Val Gly Thr Tyr Lys Phe Ile Arg Glu Glu Asp Gln Cys Ile Phe
                165                 170                 175

gag cat cgc tac ttc aaa gca aat gac act ctg ggc ttt atg ctt atg      576
Glu His Arg Tyr Phe Lys Ala Asn Asp Thr Leu Gly Phe Met Leu Met
            180                 185                 190
```

-continued

```
ttg gct gtg ctc atg gca gcc aca cat gct gtc tat ggc aag ctg cta      624
Leu Ala Val Leu Met Ala Ala Thr His Ala Val Tyr Gly Lys Leu Leu
        195                 200                 205

ctc ttc gag tat cgt cac cgc aag atg aag cca gtg cag atg gtg ccc      672
Leu Phe Glu Tyr Arg His Arg Lys Met Lys Pro Val Gln Met Val Pro
    210                 215                 220

gcc atc agc caa aac tgg aca ttc cat ggc cct ggg gct acc ggc cag      720
Ala Ile Ser Gln Asn Trp Thr Phe His Gly Pro Gly Ala Thr Gly Gln
225                 230                 235                 240

gct gct gcc aac tgg atc gct ggc ttt ggc cgt ggg ccc atg cca cca      768
Ala Ala Ala Asn Trp Ile Ala Gly Phe Gly Arg Gly Pro Met Pro Pro
                245                 250                 255

act ctg ctg ggt atc cgg cag aat ggg cat gca gct agc cgg cgg cta      816
Thr Leu Leu Gly Ile Arg Gln Asn Gly His Ala Ala Ser Arg Arg Leu
            260                 265                 270

ctg ggc atg gac gag gtc aag ggt gaa aag cag ctg ggc cga atg ttc      864
Leu Gly Met Asp Glu Val Lys Gly Glu Lys Gln Leu Gly Arg Met Phe
        275                 280                 285

tac gcg att aca ctg ctc ttc ctg ctc ctc tgg tca cca tac att gtg      912
Tyr Ala Ile Thr Leu Leu Phe Leu Leu Leu Trp Ser Pro Tyr Ile Val
    290                 295                 300

gcc tgc tac tgg cga gtg ttt gtg aaa gcc tgc gct gtg ccc cac cgc      960
Ala Cys Tyr Trp Arg Val Phe Val Lys Ala Cys Ala Val Pro His Arg
305                 310                 315                 320

tac ctg gcc act gct gtt tgg atg agc ttc gcc cag gct gct gtc aac     1008
Tyr Leu Ala Thr Ala Val Trp Met Ser Phe Ala Gln Ala Ala Val Asn
                325                 330                 335

cca atc gtc tgc ttc ctg ctt aac aag gac ctc aag aag tgc ctg agg     1056
Pro Ile Val Cys Phe Leu Leu Asn Lys Asp Leu Lys Lys Cys Leu Arg
            340                 345                 350

act cat gcc cct tgc tgg ggc aca gga ggt gcc cca gct ccc aga gaa     1104
Thr His Ala Pro Cys Trp Gly Thr Gly Gly Ala Pro Ala Pro Arg Glu
        355                 360                 365

ccc tac tgt gtc atg tga                                             1122
Pro Tyr Cys Val Met
    370


<210> SEQ ID NO 26
<211> LENGTH: 373
<212> TYPE: PRT
<213> ORGANISM: Rat coronavirus

<400> SEQUENCE: 26

Met Ala Asn Thr Thr Gly Glu Pro Glu Glu Val Ser Gly Ala Leu Ser
  1               5                  10                  15

Leu Pro Ser Ala Ser Ala Tyr Val Lys Leu Val Leu Leu Gly Leu Ile
            20                  25                  30

Met Cys Val Ser Leu Ala Gly Asn Ala Ile Leu Ser Leu Leu Val Leu
        35                  40                  45

Lys Glu Arg Ala Leu His Lys Ala Pro Tyr Tyr Phe Leu Leu Asp Leu
     50                  55                  60

Cys Leu Ala Asp Gly Ile Arg Ser Ala Ile Cys Phe Pro Phe Val Leu
 65                  70                  75                  80

Ala Ser Val Arg His Gly Ser Ser Trp Thr Phe Ser Ala Leu Ser Cys
                 85                  90                  95

Lys Ile Val Ala Phe Met Ala Val Leu Phe Cys Phe His Ala Ala Phe
            100                 105                 110

Met Leu Phe Cys Ile Ser Val Thr Arg Tyr Met Ala Ile Ala His His
        115                 120                 125
```

-continued

```
Arg Phe Tyr Ala Lys Arg Met Thr Leu Trp Thr Cys Ala Ala Val Ile
    130                 135                 140

Cys Met Ala Trp Thr Leu Ser Val Ala Met Ala Phe Pro Pro Val Phe
145                 150                 155                 160

Asp Val Gly Thr Tyr Lys Phe Ile Arg Glu Glu Asp Gln Cys Ile Phe
                165                 170                 175

Glu His Arg Tyr Phe Lys Ala Asn Asp Thr Leu Gly Phe Met Leu Met
            180                 185                 190

Leu Ala Val Leu Met Ala Ala Thr His Ala Val Tyr Gly Lys Leu Leu
        195                 200                 205

Leu Phe Glu Tyr Arg His Arg Lys Met Lys Pro Val Gln Met Val Pro
    210                 215                 220

Ala Ile Ser Gln Asn Trp Thr Phe His Gly Pro Gly Ala Thr Gly Gln
225                 230                 235                 240

Ala Ala Ala Asn Trp Ile Ala Gly Phe Gly Arg Gly Pro Met Pro Pro
                245                 250                 255

Thr Leu Leu Gly Ile Arg Gln Asn Gly His Ala Ala Ser Arg Arg Leu
            260                 265                 270

Leu Gly Met Asp Glu Val Lys Gly Glu Lys Gln Leu Gly Arg Met Phe
        275                 280                 285

Tyr Ala Ile Thr Leu Leu Phe Leu Leu Leu Trp Ser Pro Tyr Ile Val
    290                 295                 300

Ala Cys Tyr Trp Arg Val Phe Val Lys Ala Cys Ala Val Pro His Arg
305                 310                 315                 320

Tyr Leu Ala Thr Ala Val Trp Met Ser Phe Ala Gln Ala Ala Val Asn
                325                 330                 335

Pro Ile Val Cys Phe Leu Leu Asn Lys Asp Leu Lys Lys Cys Leu Arg
            340                 345                 350

Thr His Ala Pro Cys Trp Gly Thr Gly Gly Ala Pro Ala Pro Arg Glu
        355                 360                 365

Pro Tyr Cys Val Met
    370
```